US010906973B2

(12) United States Patent
Stanimirovic et al.

(10) Patent No.: US 10,906,973 B2
(45) Date of Patent: Feb. 2, 2021

(54) ANTIBODY VARIANTS TRANSMIGRATING THE BLOOD-BRAIN BARRIER AND USES THEREOF

(71) Applicants: National Research Council of Canada, Ottawa (CA); Cephalon, Inc., Frazer, PA (US)

(72) Inventors: Danica Stanimirovic, Ottawa (CA); Traian Sulea, Kirkland (CA); Kristin Kemmerich, Ottawa (CA); David Wilson, Redwood City, CA (US); Jennifer Stratton, Redwood City, CA (US); Matthew Pollard, Pullenvale (AU); Adam Clarke, Sydney (AU)

(73) Assignees: National Research Council of Canada, Ottawa (CA); Cephalon, Inc., Frazer, PA (US)

( * ) Notice: Subject to any disclaimer, the term of this patent is extended or adjusted under 35 U.S.C. 154(b) by 0 days.

(21) Appl. No.: 16/468,960

(22) PCT Filed: Dec. 12, 2017

(86) PCT No.: PCT/IB2017/057844
§ 371 (c)(1),
(2) Date: Jun. 12, 2019

(87) PCT Pub. No.: WO2018/109663
PCT Pub. Date: Jun. 21, 2018

(65) Prior Publication Data
US 2020/0095316 A1  Mar. 26, 2020

Related U.S. Application Data

(60) Provisional application No. 62/432,980, filed on Dec. 12, 2016.

(51) Int. Cl.
*C07K 16/28* (2006.01)
*A61K 47/68* (2017.01)

(52) U.S. Cl.
CPC .......... *C07K 16/28* (2013.01); *A61K 47/6803* (2017.08); *C07K 2317/32* (2013.01); *C07K 2317/33* (2013.01); *C07K 2317/52* (2013.01); *C07K 2317/565* (2013.01); *C07K 2317/569* (2013.01); *C07K 2317/92* (2013.01)

(58) Field of Classification Search
CPC .............. C07K 16/28; C07K 2317/92; C07K 2317/569; C07K 2317/565; C07K 2317/52; C07K 2317/33; C07K 2317/32; C07K 16/18; C07K 17/00; A61K 47/6803; A61K 2039/505
See application file for complete search history.

(56) References Cited

U.S. PATENT DOCUMENTS 7,943,129 B2     5/2011  Muruganandam et al.
2013/0034572 A1  2/2013  Stanimirovic et al.

FOREIGN PATENT DOCUMENTS

| WO | WO 1995/004069 A1 | 2/1995 |
| WO | WO 2002/057445 A1 | 7/2002 |
| WO | WO 2003/046560 A2 | 6/2003 |
| WO | WO 2004/076670 A1 | 9/2004 |
| WO | WO 2007/036021 A1 | 4/2007 |
| WO | WO 2011/127580 A1 | 10/2011 |
| WO | WO 2013/106577 A2 | 7/2013 |

OTHER PUBLICATIONS

PCT/IB2017/057844, Mar. 8, 2018, International Search Report and Written Opinion.
PCT/IB2017/057844, Jun. 27, 2019, International Preliminary Report on Patentability.
Farrington et al., A novel platform for engineering blood-brain barrier-crossing bispecific biologics. FASEB J. 2014;28(11):4764-4778. doi:10.1096/fj.14-253369.
Abbott, Blood-brain barrier structure and function and the challenges for CNS drug delivery. J Inherit Metab Dis. 2013;36(3):437-449. doi:10.1007/s10545-013-9608-0.
Abulrob et al., The blood-brain barrier transmigrating single domain antibody: mechanisms of transport and antigenic epitopes in human brain endothelial cells. J Neurochem. 2005;95(4):1201-1214. doi:10.1111/j.1471-4159.2005.03463.x.
Arbabi Ghahroudi et al., Selection and identification of single domain antibody fragments from camel heavy-chain antibodies. FEBS Lett. 1997;414(3):521-526. doi:10.1016/s0014-5793(97)01062-4.
Bell et al., Differential tumor-targeting abilities of three single-domain antibody formats. Cancer Lett. 2010;289(1):81-90. doi:10.1016/j.canlet.2009.08.003.
Chothia et al., Canonical structures for the hypervariable regions of immunoglobulins. J Mol Biol. 1987;196(4):901-917. doi:10.1016/0022-2836(87)90412-8.
Davies et al., Affinity improvement of single antibody VH domains: residues in all three hypervariable regions affect antigen binding. Immunotechnology. Sep. 1996;2(3):169-79. doi: 10.1016/S1380-2933(96)00045-0.
De Kruif et al., Leucine zipper dimerized bivalent and bispecific scFv antibodies from a semisynthetic antibody phage display library. J Biol Chem. 1996;271(13):7630-7634. doi:10.1074/jbc.271.13.7630.

(Continued)

*Primary Examiner* — Kimberly Ballard
*Assistant Examiner* — Stacey N Macfarlane
(74) *Attorney, Agent, or Firm* — Wolf, Greenfield & Sacks, P.C.

(57) ABSTRACT

The present invention relates, in general, to polypeptides capable of transmigrating the blood-brain barrier, and uses thereof. More specifically, the present invention relates to polypeptides derived by site-directed mutagenesis of an existing antibody fragment and uses thereof, and methods of making such molecules. The polypeptides of the present invention show enhanced blood-brain barrier crossing and brain exposure levels in vitro and in vivo.

19 Claims, 13 Drawing Sheets

Specification includes a Sequence Listing.

(56) References Cited

OTHER PUBLICATIONS

Demeule et al., Involvement of the low-density lipoprotein receptor-related protein in the transcytosis of the brain delivery vector angiopep-2. J Neurochem. 2008;106(4):1534-1544. doi:10.1111/j.1471-4159.2008.05492.x.

Dumoulin et al., Single-domain antibody fragments with high conformational stability. Protein Sci. 2002;11(3):500-515. doi:10.1110/ps.34602.

Eisenberg et al., Analysis of membrane and surface protein sequences with the hydrophobic moment plot. J Mol Biol. 1984;179(1):125-142. doi:10.1016/0022-2836(84)90309-7.

Erdlenbruch et al., Alkylglycerol opening of the blood-brain barrier to small and large fluorescence markers in normal and C6 glioma-bearing rats and isolated rat brain capillaries. Br J Pharmacol. 2003;140(7):1201-1210. doi:10.1038/sj.bjp.0705554.

Gan et al., Gene delivery with viral vectors for cerebrovascular diseases. Front Biosci (Elite Ed). Jan. 1, 2013; 5: 188-203. EPub Jan. 1, 2013.

Garberg et al., in vitro models for the blood-brain barrier. Toxicol in Vitro. 2005;19(3):299334. doi:10.1016/j.tiv.2004.06.011.

Gergov et al., Simultaneous screening for 238 drugs in blood by liquid chromatography-ionspray tandem mass spectrometry with multiple-reaction monitoring. J Chromatog B. Sep. 25, 2003;795(1):41-53. doi: 10.1016/S1570-0232(03)00498-7.

Gonzales et al., Minimizing the Immunogenicity of Antibodies for Clinical Application. Tumor Biol. 2005;26:31-43. doi: 10.1159/000084184.

Gottesman et al., Biochemistry of multidrug resistance mediated by the multidrug transporter. Annu Rev Biochem. 1993;62:385-427. doi:10.1146/annurev.bi.62.070193.002125.

Guillaume et al., Intra-arterial chemotherapy with osmotic blood-brain barrier disruption for aggressive oligodendroglial tumors: results of a phase I study. Neurosurgery. 2010;66(1):48-58. doi:10.1227/01.

Hamers-Casterman et al., Naturally occurring antibodies devoid of light chains. Nature. 1993;363(6428):446-448. doi:10.1038/363446a0.

Haqqani et al., Multiplexed evaluation of serum and CSF pharmacokinetics of brain-targeting single-domain antibodies using a NanoLC-SRM-ILIS method. Mol Pharm. 2013;10(5):15421556. doi:10.1021/mp3004995.

Huang et al., A new approach for multiple sampling of cisternal cerebrospinal fluid in rodents with minimal trauma and inflammation. J Neurosci Meth. Dec. 1995;63(1-2):13-22. doi: 10.1016/0165-0270(95)00080-1.

Hussack et al., Engineered single-domain antibodies with high protease resistance and thermal stability. PLoS One. 2011;6(11):e28218. doi:10.1371/journal.pone.0028218.

Hussack et al., Neutralization of Clostridium difficile toxin a with single-domain antibodies targeting the cell receptor binding domain. J Biol Chem. 2011;286(11):8961-8976. doi:10.1074/jbc.M110.198754.

Iqbal et al., Kinetic analysis of novel mono- and multivalent Vhh-fragments and their application for molecular imaging of brain tumours. Br J Pharmacol. 2010;160(4):1016-1028. doi:10.1111/j.1476-5381.2010.00742.x.

Jespers et al., Aggregation-resistant domain antibodies selected on phage by heat denaturation. Nat Biotechnol. 2004;22(9):1161-1165. doi:10.1038/nbt1000.

Jones et al., Replacing the complementarity-determining regions in a human antibody with those from a mouse. Nature. 1986;321(6069):522-525. doi:10.1038/321522a0.

Kabat et al., Identical V region amino acid sequences and segments of sequences in antibodies of different specificities. Relative contributions of VH and VL genes, minigenes, and complementarity-determining regions to binding of antibody-combining sites. J Immunol. 1991;147(5):1709-1719.

Kim et al., Disulfide linkage engineering for improving biophysical properties of human VH domains. Protein Eng Des Sel. 2012;25(10):581-89. Epub Aug. 30, 2012. doi: 10.1093/protein/gzs055.

Kornhuber et al., A method for repeated CSF sampling in the freely moving rat. J Neurosci Meth. Jul. 1986:17(0:63-68. doi: 10.1016/0165-0270(86)90035-X.

Li et al., Pentabody-mediated antigen delivery induces antigen-specific mucosal immune response. Mol Immunol. 2009;46(8-9):1718-1726. doi:10.1016/j.molimm.2009.02.007.

Merritt et al., AB5 toxins. Curr Opin Struct Biol. 1995;5(2):165-171. doi:10.1016/0959-440x(95)80071-9.

Muruganandam et al., Selection of phage-displayed llama single-domain antibodies that transmigrate across human blood-brain barrier endothelium. FASEB J. 2002;16(2):240-242. doi:10.1096/fj.01-0343fje.

Nhan et al., Drug delivery to the brain by focused ultrasound induced blood-brain barrier disruption: quantitative evaluation of enhanced permeability of cerebral vasculature using two-photon microscopy. J Control Release. 2013;172(1):274-280. doi:10.1016/j.jconrel.2013.08.029.

Nicaise et al., Affinity transfer by CDR grafting on a nonimmunoglobulin scaffold. Protein Sci. Jul. 2004; 13(7): 1882-1891. doi: 10.1110/ps.03540504.

Nielsen et al., Targeting of Bivalent Anti-ErbB2 Diabody Antibody Fragments to Tumor Cells Is Independent of the Intrinsic Antibody Affinity. Canc Res. Nov. 15, 2000;60(22):6434-6440.

Nuttall et al., Isolation and characterization of an IgNAR variable domain specific for the human mitochondrial translocase receptor Tom70. Eur J Biochem. 2003;270(17):3543-3554. doi:10.1046/j.1432-1033.2003.03737.x.

Padlan, A possible procedure for reducing the immunogenicity of antibody variable domains while preserving their ligand-binding properties. Mol Immunol. 1991;28(4-5):489-498. doi:10.1016/0161-5890(91)90163-e.

Pardridge et al., Selective transport of an anti-transferrin receptor antibody through the blood-brain barrier in vivo. J Pharmacol Exp Ther. 1991;259(1):66-70.

Pardridge, Drug and gene delivery to the brain: the vascular route. Neuron. 2002;36(4):555558. doi:10.1016/s0896-6273(02)01054-1.

Pardridge, Transport of small molecules through the blood-brain barrier: biology and methodology. Adv Drug Del Rev. Jul. 1995:15 (1-3):5-36. doi: 10.1016/0169-409X(95)00003-P.

Preston et al., Graded reversible opening of the rat blood-brain barrier by intracarotid infusion of sodium caprate. J Neurosci Meth. Mar. 15, 2008;168(20:443-9. doi: 10.1016/j.jneumeth.2007.11.004.

Queen et al., A humanized antibody that binds to the interleukin 2 receptor. Proc Natl Acad Sci U S A. 1989;86(24):10029-10033. doi:10.1073/pnas.86.24.10029.

Ridgway et al., 'Knobs-into-holes' engineering of antibody CH3 domains for heavy chain heterodimerization. Protein Eng. 1996;9(7):617-621. doi:10.1093/protein/9.7.617.

Riechmmann et al., Reshaping human antibodies for therapy. Nature. 1988;332(6162):323327. doi:10.1038/332323a0.

Samuels et al., Modulation of vinblastine resistance with cyclosporine: A phase I study. J Clin Pharmacol. Oct. 1993;54(4):421-429. doi: 10.1038/clpt.1993.169.

Sumbria et al., Pharmacokinetics and brain uptake of an IgG-TNF decoy receptor fusion protein following intravenous, intraperitoneal, and subcutaneous administration in mice. Mol Pharm. 2013;10(4):1425-1431.

Tempest et al., Reshaping a human monoclonal antibody to inhibit human respiratory syncytial virus infection in vivo. Biotechnology (N Y). 1991;9(3):266-271. doi:10.1038/nbt0391-266.

To et al., Isolation of monomeric human V(H)s by a phage selection. J Biol Chem. 2005;280(50):41395-41403. doi:10.1074/jbc.M509900200.

Tsurushita et al., Design of humanized antibodies: from anti-Tac to Zenapax. Methods. 2005;36(1):69-83. doi:10.1016/j.ymeth.2005.01.007.

(56) References Cited

OTHER PUBLICATIONS

Watanabe et al., Comparative study on reversal efficacy of SDZ PSC 833, cyclosporin A and verapamil on multidrug resistance in vitro and in vivo. Acta Oncol. 1995;34(2):235-241. doi:10.3109/02841869509093961.

Xiao et al., Receptor-mediated endocytosis and brain delivery of therapeutic biologics. Int J Cell Biol. 2013;2013:703545. doi:10.1155/2013/703545.

Yaksh et al., Chronic catheterization of the spinal subarachnoid space. Physiol Behay. 1976;17(6):1031-1036. doi:10.1016/0031-9384(76)90029-9.

Yu et al., Boosting brain uptake of a therapeutic antibody by reducing its affinity for a transcytosis target. Sci Transl Med. 2011;3(84):84ra44. doi:10.1126/scitranslmed.3002230.

Zhu et al., Combody: one-domain antibody multimer with improved avidity Biol. 2010;88(6):667-675. doi:10.1038/icb.2010.21. Immunol Cell.

```
FC5     DVQLQASGGGLVQAGGSLRLSCAASGFKITHYTMGWFRQAPGKEREFVS
FC5-H7  EVQLVESGGGLVQPGGSLRLSCAASGFKITHYTMGWFRQAPGKEREFVS
D56K    EVQLVESGGGLVQPGGSLRLSCAASGFKITHYTMGWFRQAPGKEREFVS
N57D    EVQLVESGGGLVQPGGSLRLSCAASGFKITHYTMGWFRQAPGKEREFVS
F59I    EVQLVESGGGLVQPGGSLRLSCAASGFKITHYTMGWFRQAPGKEREFVS
F59L    EVQLVESGGGLVQPGGSLRLSCAASGFKITHYTMGWFRQAPGKEREFVS
T105K   EVQLVESGGGLVQPGGSLRLSCAASGFKITHYTMGWFRQAPGKEREFVS

FC5     RITWGGDNTFYSNSVKGRFTISRDNAKMTVYLQMNSLKPEDTADYCAA
FC5-H7  RITWGGDNTFYSNSVKGRFTISRDNSKNTLYLQMNSLRAEDTAVYYCAA
D56K    RITWGGKNTFYSNSVKGRFTISRDNSKNTLYLQMNSLRAEDTAVYYCAA
N57D    RITWGGDDTFYSNSVKGRFTISRDNSKNTLYLQMNSLRAEDTAVYYCAA
F59I    RITWGGDNTIYSNSVKGRFTISRDNSKNTLYLQMNSLRAEDTAVYYCAA
F59L    RITWGGDNTLYSNSVKGRFTISRDNSKNTLYLQMNSLRAEDTAVYYCAA
T105K   RITWGGDNTFYSNSVKGRFTISRDNSKNTLYLQMNSLRAEDTAVYYCAA

FC5     GSTSTATPLRVDYWGKGTQVTVSS     SEQ ID NO:16
FC5-H7  GSTSTATPLRVDYWGQGTLVTVSS     SEQ ID NO:17
D56K    GSTSTATPLRVDYWGQGTLVTVSS     SEQ ID NO:12
N57D    GSTSTATPLRVDYWGQGTLVTVSS     SEQ ID NO:13
F59I    GSTSTATPLRVDYWGQGTLVTVSS     SEQ ID NO:14
F59L    GSTSTATPLRVDYWGQGTLVTVSS     SEQ ID NO:15
T105K   GSTSTAKPLRVDYWGQGTLVTVSS     SEQ ID NO:11
```

FIG. 7

SEQUENCE LISTING

<160> NUMBER OF SEQ ID NOS: 35

<210> SEQ ID NO 1
<211> LENGTH: 10
<212> TYPE: PRT
<213> ORGANISM: Artificial Sequence
<220> FEATURE:
<223> OTHER INFORMATION: CDR1 FC5

<400> SEQUENCE: 1

Gly Phe Lys Ile Thr His Tyr Thr Met Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2 consensus
<220> FEATURE:
<221> NAME/KEY: misc_feature
<222> LOCATION: (7)..(7)
<223> OTHER INFORMATION: where X is D or K
<220> FEATURE:
<221> NAME/KEY: misc_feature
<222> LOCATION: (8)..(8)
<223> OTHER INFORMATION: where X is N or D
<220> FEATURE:
<221> NAME/KEY: misc_feature
<222> LOCATION: (10)..(10)
<223> OTHER INFORMATION: where X is F, I or L

<400> SEQUENCE: 2

Arg Ile Thr Trp Gly Gly Xaa Xaa Thr Xaa Tyr Ser Asn Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: CDR3 consensus
<220> FEATURE:
<221> NAME/KEY: misc_feature
<222> LOCATION: (7)..(7)
<223> OTHER INFORMATION: where X is T or K

<400> SEQUENCE: 3

Gly Ser Thr Ser Thr Ala Xaa Pro Leu Arg Val Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: CDR2 FC5

<400> SEQUENCE: 4

Arg Ile Thr Trp Gly Gly Asp Asn Thr Phe Tyr Ser Asn Ser Val Lys
1               5                   10                  15

Gly

<210> SEQ ID NO 5
<211> LENGTH: 17
<212> TYPE: PRT
<213> ORGANISM: Artificial Sequence

<220> FEATURE:
<223> OTHER INFORMATION: CDR2 D56K

<400> SEQUENCE: 5

Arg Ile Thr Trp Gly Gly Lys Asn Thr Phe Tyr Ser Asn Ser Val Lys
1               5                   10                  15
Gly

<210> SEQ ID NO 6
<211> LENGTH: 17
<212> TYPE: PRT
<213> ORGANISM: Artificial Sequence
<220> FEATURE:
<223> OTHER INFORMATION: CDR2 N57D

<400> SEQUENCE: 6

Arg Ile Thr Trp Gly Gly Asp Asp Thr Phe Tyr Ser Asn Ser Val Lys
1               5                   10                  15
Gly

<210> SEQ ID NO 7
<211> LENGTH: 17
<212> TYPE: PRT
<213> ORGANISM: Artificial Sequence
<220> FEATURE:
<223> OTHER INFORMATION: CDR2 F59I

<400> SEQUENCE: 7

Arg Ile Thr Trp Gly Gly Asp Asn Thr Ile Tyr Ser Asn Ser Val Lys
1               5                   10                  15
Gly

<210> SEQ ID NO 8
<211> LENGTH: 17
<212> TYPE: PRT
<213> ORGANISM: Artificial Sequence
<220> FEATURE:
<223> OTHER INFORMATION: CDR2 F59L

<400> SEQUENCE: 8

Arg Ile Thr Trp Gly Gly Asp Asn Thr Leu Tyr Ser Asn Ser Val Lys
1               5                   10                  15
Gly

<210> SEQ ID NO 9
<211> LENGTH: 13
<212> TYPE: PRT
<213> ORGANISM: Artificial Sequence
<220> FEATURE:
<223> OTHER INFORMATION: CDR3 T105K

<400> SEQUENCE: 9

Gly Ser Thr Ser Thr Ala Lys Pro Leu Arg Val Asp Tyr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: CDR3 FC5

<400> SEQUENCE: 10

Gly Ser Thr Ser Thr Ala Thr Pro Leu Arg Val Asp Tyr

```
1               5                   10
```

<210> SEQ ID NO 11
<211> LENGTH: 122
<212> TYPE: PRT
<213> ORGANISM: Artificial Sequence
<220> FEATURE:
<223> OTHER INFORMATION: FC5-H7-T105K

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Lys Pro Leu Arg Val Asp Tyr Trp
            100                 105                 110

Gly Gln Gly Thr Leu Val Thr Val Ser Ser
            115                 120

<210> SEQ ID NO 12
<211> LENGTH: 122
<212> TYPE: PRT
<213> ORGANISM: Artificial Sequence
<220> FEATURE:
<223> OTHER INFORMATION: FC5-H7-D56K

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Lys Asn Thr Phe Tyr Ser Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
            115                 120

<210> SEQ ID NO 13
<211> LENGTH: 122
<212> TYPE: PRT
<213> ORGANISM: Artificial Sequence
<220> FEATURE:
<223> OTHER INFORMATION: FC5-H7-N57D

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Thr Phe Tyr Ser Asn Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120

<210> SEQ ID NO 14
<211> LENGTH: 122
<212> TYPE: PRT
<213> ORGANISM: Artificial Sequence
<220> FEATURE:
<223> OTHER INFORMATION: FC5-H7-F59I

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Ile Tyr Ser Asn Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120

<210> SEQ ID NO 15
<211> LENGTH: 122
<212> TYPE: PRT
<213> ORGANISM: Artificial Sequence
<220> FEATURE:
<223> OTHER INFORMATION: FC5-H7-F59L

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Leu Tyr Ser Asn Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Gly Ser Thr Ser Thr Ala Thr Pro Leu Arg Val Asp Tyr Trp
                100                 105                 110

Gly Gln Gly Thr Leu Val Thr Val Ser Ser
            115                 120

<210> SEQ ID NO 16
<211> LENGTH: 122
<212> TYPE: PRT
<213> ORGANISM: Artificial Sequence
<220> FEATURE:
<223> OTHER INFORMATION: FC5

<400> SEQUENCE: 16

Asp Val Gln Leu Gln Ala Ser Gly Gly Gly Leu Val Gln Ala Gly Gly
 1               5                  10                  15

Ser Leu Arg Leu Ser Cys Ala Ala Ser Gly Phe Lys Ile Thr His Tyr
                20                  25                  30

Thr Met Gly Trp Phe Arg Gln Ala Pro Gly Lys Glu Arg Glu Phe Val
             35                  40                  45

Ser Arg Ile Thr Trp Gly Gly Asp Asn Thr Phe Tyr Ser Asn Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Asp Tyr Tyr Cys
                 85                  90                  95

Ala Ala Gly Ser Thr Ser Thr Ala Thr Pro Leu Arg Val Asp Tyr Trp
                100                 105                 110

Gly Lys Gly Thr Gln Val Thr Val Ser Ser
            115                 120

<210> SEQ ID NO 17
<211> LENGTH: 122
<212> TYPE: PRT
<213> ORGANISM: Artificial Sequence
<220> FEATURE:
<223> OTHER INFORMATION: FC5-H7

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Lys Ile Thr His Tyr
                20                  25                  30

Thr Met Gly Trp Phe Arg Gln Ala Pro Gly Lys Glu Arg Glu Phe Val
             35                  40                  45

Ser Arg Ile Thr Trp Gly Gly Asp Asn Thr Phe Tyr Ser Asn Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Gly Ser Thr Ser Thr Ala Thr Pro Leu Arg Val Asp Tyr Trp
                100                 105                 110
```

Gly Gln Gly Thr Leu Val Thr Val Ser Ser
        115                 120

<210> SEQ ID NO 18
<211> LENGTH: 30
<212> TYPE: DNA
<213> ORGANISM: Artificial Sequence
<220> FEATURE:
<223> OTHER INFORMATION: fdTGIII primer

<400> SEQUENCE: 18
gtgaaaaaat tattattatt cgcaattcct                              30

<210> SEQ ID NO 19
<211> LENGTH: 20
<212> TYPE: DNA
<213> ORGANISM: Artificial Sequence
<220> FEATURE:
<223> OTHER INFORMATION: 96GIII primer

<400> SEQUENCE: 19
ccctcatagt tagcgtaacg                                         20

<210> SEQ ID NO 20
<211> LENGTH: 15
<212> TYPE: PRT
<213> ORGANISM: Artificial Sequence
<220> FEATURE:
<223> OTHER INFORMATION: FC5 peptide

<400> SEQUENCE: 20

Ile Thr Trp Gly Gly Asp Asn Thr Phe Tyr Ser Asn Ser Val Lys
1               5                   10                  15

<210> SEQ ID NO 21
<211> LENGTH: 9
<212> TYPE: PRT
<213> ORGANISM: Artificial Sequence
<220> FEATURE:
<223> OTHER INFORMATION: A20.1 peptide

<400> SEQUENCE: 21

Thr Thr Tyr Tyr Ala Asp Ser Val Lys
1               5

<210> SEQ ID NO 22
<211> LENGTH: 11
<212> TYPE: PRT
<213> ORGANISM: Artificial Sequence
<220> FEATURE:
<223> OTHER INFORMATION: A20.1 peptide

<400> SEQUENCE: 22

Glu Phe Val Ala Ala Gly Ser Ser Thr Gly Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: A20.1 peptide

<400> SEQUENCE: 23

Thr Phe Ser Met Asp Pro Met Ala Trp Phe Arg
1               5                   10

<210> SEQ ID NO 24
<211> LENGTH: 26
<212> TYPE: PRT
<213> ORGANISM: Artificial Sequence
<220> FEATURE:
<223> OTHER INFORMATION: A20.1 peptide

<400> SEQUENCE: 24

```
Asp Glu Tyr Ala Tyr Trp Gly Gln Gly Thr Gln Val Thr Val Ser Ser
1               5                   10                  15

Gly Gln Ala Gly Gln Gly Ser Glu Gln Lys
            20                  25
```

<210> SEQ ID NO 25
<211> LENGTH: 9
<212> TYPE: PRT
<213> ORGANISM: Artificial Sequence
<220> FEATURE:
<223> OTHER INFORMATION: FC5-H7 variant peptide

<400> SEQUENCE: 25

```
Leu Ser Cys Ala Ala Ser Gly Phe Lys
1               5
```

<210> SEQ ID NO 26
<211> LENGTH: 11
<212> TYPE: PRT
<213> ORGANISM: Artificial Sequence
<220> FEATURE:
<223> OTHER INFORMATION: FC5-H7 variant peptide

<400> SEQUENCE: 26

```
Asn Thr Leu Tyr Leu Gln Met Asn Ser Leu Arg
1               5                   10
```

<210> SEQ ID NO 27
<211> LENGTH: 19
<212> TYPE: PRT
<213> ORGANISM: Artificial Sequence
<220> FEATURE:
<223> OTHER INFORMATION: FC5-H7 variant peptide

<400> SEQUENCE: 27

```
Glu Val Gln Leu Val Glu Ser Gly Gly Gly Leu Val Gln Pro Gly Gly
1               5                   10                  15

Ser Leu Arg
```

<210> SEQ ID NO 28
<211> LENGTH: 14
<212> TYPE: PRT
<213> ORGANISM: Artificial Sequence
<220> FEATURE:
<223> OTHER INFORMATION: Albumin peptide

<400> SEQUENCE: 28

```
Ala Pro Gln Val Ser Thr Pro Thr Leu Val Glu Ala Ala Arg
1               5                   10
```

<210> SEQ ID NO 29
<211> LENGTH: 232
<212> TYPE: PRT
<213> ORGANISM: Artificial Sequence
<220> FEATURE:
<223> OTHER INFORMATION: IgG1 Fc

<400> SEQUENCE: 29

Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Gly Pro Glu Val Lys Phe Asn Trp His
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Gly Leu His Asn His Tyr Thr Gln
210                 215                 220

Lys Ser Leu Ser Leu Ser Pro Gly
225                 230

<210> SEQ ID NO 30
<211> LENGTH: 366
<212> TYPE: DNA
<213> ORGANISM: Artificial Sequence
<220> FEATURE:
<223> OTHER INFORMATION: FC5-H7-T105K

<400> SEQUENCE: 30

```
gaggtccagc tggtggaatc tggaggagga ttggtgcagc cggggggctc tctgagactc      60
tcctgtgcag cctctggatt caaaatcact cactatacca tgggctggtt ccgccaggct     120
ccagggaagg agcgtgaatt tgtatcacgt attacttggg gtggtgataa caccttctat     180
tcaaactccg tgaagggccg attcaccatt tccagagaca cagcaagaa cacgctgtat      240
ctgcaaatga acagcctgcg tgcggaggac acggccgtgt attactgtgc agcaggttcg     300
acgtcgactg cgaaaccact agggtggac tactggggcc aggggaccct ggtcaccgtc     360
tcctca                                                               366
```

<210> SEQ ID NO 31
<211> LENGTH: 366
<212> TYPE: DNA
<213> ORGANISM: Artificial Sequence
<220> FEATURE:
<223> OTHER INFORMATION: FC5-H7-D56K

<400> SEQUENCE: 31

```
gaggtccagc tggtggaatc tggaggagga ttggtgcagc cggggggctc tctgagactc    60
tcctgtgcag cctctggatt caaaatcact cactatacca tgggctggtt ccgccaggct   120
ccagggaagg agcgtgaatt tgtatcacgt attacttggg gtggtaaaaa caccttctat   180
tcaaactccg tgaagggccg attcaccatt tccagagaca acagcaagaa cacgctgtat   240
ctgcaaatga acagcctgcg tgcggaggac acggccgtgt attactgtgc agcaggttcg   300
acgtcgactg cgacgccact tagggtggac tactggggcc aggggaccct ggtcaccgtc   360
tcctca                                                              366
```

```
<210> SEQ ID NO 32
<211> LENGTH: 366
<212> TYPE: DNA
<213> ORGANISM: Artificial Sequence
<220> FEATURE:
<223> OTHER INFORMATION: FC5-H7-N57D

<400> SEQUENCE: 32
gaggtccagc tggtggaatc tggaggagga ttggtgcagc cggggggctc tctgagactc    60
tcctgtgcag cctctggatt caaaatcact cactatacca tgggctggtt ccgccaggct   120
ccagggaagg agcgtgaatt tgtatcacgt attacttggg gtggtgatga taccttctat   180
tcaaactccg tgaagggccg attcaccatt tccagagaca acagcaagaa cacgctgtat   240
ctgcaaatga acagcctgcg tgcggaggac acggccgtgt attactgtgc agcaggttcg   300
acgtcgactg cgacgccact tagggtggac tactggggcc aggggaccct ggtcaccgtc   360
tcctca                                                              366
```

```
<210> SEQ ID NO 33
<211> LENGTH: 366
<212> TYPE: DNA
<213> ORGANISM: Artificial Sequence
<220> FEATURE:
<223> OTHER INFORMATION: FC5-H7-F59I

<400> SEQUENCE: 33
gaggtccagc tggtggaatc tggaggagga ttggtgcagc cggggggctc tctgagactc    60
tcctgtgcag cctctggatt caaaatcact cactatacca tgggctggtt ccgccaggct   120
ccagggaagg agcgtgaatt tgtatcacgt attacttggg gtggtgataa caccatctat   180
tcaaactccg tgaagggccg attcaccatt tccagagaca acagcaagaa cacgctgtat   240
ctgcaaatga acagcctgcg tgcggaggac acggccgtgt attactgtgc agcaggttcg   300
acgtcgactg cgacgccact tagggtggac tactggggcc aggggaccct ggtcaccgtc   360
tcctca                                                              366
```

```
<210> SEQ ID NO 34
<211> LENGTH: 366
<212> TYPE: DNA
<213> ORGANISM: Artificial Sequence
<220> FEATURE:
<223> OTHER INFORMATION: FC5-H7-F59L

<400> SEQUENCE: 34
gaggtccagc tggtggaatc tggaggagga ttggtgcagc cggggggctc tctgagactc    60
tcctgtgcag cctctggatt caaaatcact cactatacca tgggctggtt ccgccaggct   120
ccagggaagg agcgtgaatt tgtatcacgt attacttggg gtggtgataa caccctgtat   180
```

```
tcaaactccg tgaagggccg attcaccatt tccagagaca acagcaagaa cacgctgtat      240
ctgcaaatga acagcctgcg tgcggaggac acggccgtgt attactgtgc agcaggttcg      300
acgtcgactg cgacgccact tagggtggac tactggggcc aggggaccct ggtcaccgtc      360
tcctca                                                                  366

<210> SEQ ID NO 35
<211> LENGTH: 366
<212> TYPE: DNA
<213> ORGANISM: Artificial Sequence
<220> FEATURE:
<223> OTHER INFORMATION: FC5-H7

<400> SEQUENCE: 35
gaggtccagc tggtggaatc tggaggagga ttggtgcagc cggggggctc tctgagactc       60
tcctgtgcag cctctggatt caaaatcact cactatacca tgggctggtt ccgccaggct      120
ccagggaagg agcgtgaatt tgtatcacgt attacttggg gtggtgataa caccttctat      180
tcaaactccg tgaagggccg attcaccatt tccagagaca acagcaagaa cacgctgtat      240
ctgcaaatga acagcctgcg tgcggaggac acggccgtgt attactgtgc agcaggttcg      300
acgtcgactg cgacgccact tagggtggac tactggggcc aggggaccct ggtcaccgtc      360
tcctca                                                                  366
```

ANTIBODY VARIANTS TRANSMIGRATING THE BLOOD-BRAIN BARRIER AND USES THEREOF

RELATED APPLICATIONS

This application is a national stage filing under 35 U.S.C. § 371 of International Patent Application Serial No. PCT/IB2017/057844 filed on Dec. 12, 2017, which claims benefit from U.S. Provisional Application No. 62/432,980 filed on Dec. 12, 2016, the contents of each of which are incorporated herein by reference.

FIELD OF THE INVENTION

The present invention relates to antibody fragments that transmigrate the blood-brain barrier, and uses thereof. More specifically, the present invention relates to antibody fragments derived by point-mutation of an existing antibody fragments and uses thereof; the antibody fragments of the present invention show enhanced binding to brain endothelial cells or enhanced transmigration across the blood-brain barrier.

BACKGROUND OF THE INVENTION

Neurodegenerative diseases, such as Alzheimer's and Parkinson's disease, are an increasing burden on our ageing society because there are currently no effective treatments for these disabling conditions. Treatment as well as early diagnosis of these and other diseases that originate in the brain remain challenging because the majority of suitable therapeutic molecules and diagnostics cannot penetrate the tight and highly restrictive blood-brain barrier (BBB) (Abbott, 2013). The BBB constitutes a physical barricade that is formed by brain endothelial cells (BECs) that line the blood vessels and connect with each other through tight junctions (Abbott, 2013). The tight junctions formed between the BECs are essential for the integrity of the BBB and prevent the paracellular transport of hydrophilic molecules larger than 500 daltons (Da). Because brain endothelial cells exhibit very low pinocytosis rates (Abbott, 2013), transcellular transport of larger molecules is limited to the highly specific receptor mediated transcytosis (RMT) pathway, and the passive, charge-based adsorption mediated transcytosis (Abbott, 2013; Pardridge, 2002). Additionally, the high density of efflux pumps, such as P-glycoprotein or the multi-drug resistance protein-1 (MDR-1), contribute to the removal of unwanted substances from the brain (Abbott, 2013).

While all these characteristics protect the brain from pathogens and toxins, they equally prevent the entry of most therapeutics. In fact, less than 5% of small molecule therapeutics and virtually none of the larger therapeutics can cross the BBB in pharmacologically relevant concentrations (i.e., sufficient to engage a central nervous system (CNS) target and elicit pharmacologic/therapeutic response) unless they are specifically 'ferried', that is, coupled to a transporter molecule. Due to the lack of effective 'carriers' to transport molecules across the BBB, numerous drugs against neurodegenerative diseases have been 'shelved' or eliminated from further development as they cannot be delivered to the brain in sufficient amount.

Different approaches to deliver larger molecules into the brain have been explored. For example, the integrity of the BBB may be disrupted, resulting in a leaky BBB, which in turn allows for unrestricted, paracellular entry of larger molecules into the brain. Tight junctions can be successfully loosened or disrupted by various approaches. For example, injection of substances that induce osmotic shock (for example, mannitol, hypertonic solutions) into the blood stream causes cell shrinkage and results in the disruption of tight junctions, therefore severely compromising the BBB (Guillaume, 2010). Other modulators of tight junctions include alkylglycerols, bradykinin and several analogues thereof, as well as viruses that modulate expression of proteins involved in maintaining the tight junctions (Erdlenbruch et al., 2003; Preston et al., 2008; Gan et al., 2013). A more localized disruption of the BBB is possible through the application of focused ultrasound (Nhan et al., 2013). However, the periods during which the BBB is disrupted are sufficient to alter brain homeostasis and allow harmful chemicals, toxins and pathogens to enter the brain; this could result in serious side-effects, e.g., seizures and brain swelling, infection and possibly permanent neuropathological changes. Therefore, repeated treatments with these techniques for chronic and diffuse brain diseases affecting multiple brain regions are not practical. Most of these treatments are costly, necessitate hospitalization, and some approaches require anesthesia.

Another approach for circumventing the BBB is direct injection of therapeutic molecules into the cerebrospinal fluid (CSF), the parenchymal space, or other parts of the brain. Several delivery methods have been developed, including: intracerebral (intra-parenchymal), intraventricular, and intrathecal delivery via infusion or convection-enhanced diffusion (CED) pumps. However, any type of direct injection into the brain or intracerebral implant is an invasive and costly procedure, as it requires hospitalization, anesthesia, and often surgery. Moreover, the poor diffusion rates of the therapeutics, particularly large biologics, within brain parenchyma limit the penetration of therapeutics to only small areas surrounding the site of injection/implantation. The correct placement of injections, catheters, and implants is challenging yet crucial to achieve diffusion of the drug to the targeted region of the brain. Additionally, catheters and implants provide a site for infection and/or immune response against the foreign material.

In another attempt to increase delivery across the BBB, CNS drugs have been modified to increase their brain uptake. Such modifications can include a change of their surface charge, a reduction in molecule size, and change to the lipophilicity of the drugs. However, any modifications to increase brain penetration are also likely to alter the overall pharmacology of the drug, including its desired activity and/or specificity. In addition, lipophilic molecules are more prone to being exported from the brain through the P-glycoprotein efflux pump.

Finally, endogenous transport mechanisms across the BBB have been exploited. Physiological mechanisms that allow transport of large molecules across the BBB can be divided into the highly specific receptor mediated transcytosis (RMT) and the non-specific charge based adsorptive mediated endocytosis pathways. Endocytosis is triggered upon binding of the specific ligand to its receptor, or upon electrostatic interaction between the cationic ligand or drug and the anionic functional groups on the brain endothelial cell surface (luminal side), respectively. Subsequently, the newly formed endosome is transcytosed across the cell to the abluminal side, to release its cargo.

Because adsorptive mediated transcytosis is non-specific, charge-mediated interaction, it occurs in all vascular beds and organs, limiting the availability of drug for brain delivery. Therefore, exploiting the RMT pathway remains the only physiological, non-invasive yet highly receptor-specific brain delivery method.

Only a few receptors are presently known to undergo RMT at the BBB and 'ferry' across their natural ligands: the well-studied transferrin receptor (TfR), the insulin receptor (IR), low-density lipoprotein receptor related proteins 1 and 2 (LRP-1 and -2) and diphtheria toxin receptor Peptides, natural ligands, and antibodies or antibody fragments have been developed that bind to these receptors (Pardridge et al., 1991; Yu et al., 2011; Muruganandam et al., 2001; Abulrob et al., 2005; Demeule, 2008; Sumbria et al., 2013), functioning as blood-to-brain transporters that utilize endogenous RMT pathways. Recently, antibodies against CD98hc, a component of the large neutral amino acid transporter (LAT1), have been shown to undergo transcytosis across the BBB, suggesting that this transporter could be another target for developing BBB carriers. However, to date only a single peptide (Angiopep ANG1005, targeting LRP-1) has been analyzed in phase I clinical studies, while other candidates are being studied in laboratory settings. The RMT pathway appears to be the most promising pathway for transport of biologic drugs into the brain, but current approaches have limitations, including: non-selective expression of the target receptor at the BBB compared to the vascular endothelium in other organs, competition between the carrier and the natural ligands to the receptor, ineffective transcytosis of a receptor as well as lysosomal degradation of endocytosed carriers (Xiao and Gun, 2013).

The lack of high-capacity and high-selectivity BBB carriers delays the development of new therapeutics and diagnostics for diseases originating in the brain, including brain tumors and neurodegenerative diseases.

SUMMARY OF THE INVENTION

The present invention relates to antibody fragments that transmigrate the blood-brain barrier, and uses thereof. More specifically, the present invention relates to antibody fragments derived by point-mutation of existing antibody fragments and uses thereof; the antibody fragments of the present invention show enhanced transmigration across the blood-brain barrier.

The present invention provides an isolated or purified antibody fragment, comprising:
  a complementarity determining region (CDR) 1 sequence of GFKITHYTMG (SEQ ID NO:1);
  a CDR2 sequence of RITWGGX$_1$X$_2$TX$_3$YSNSVKG (SEQ ID NO:2), where X$_1$ is D or K, X$_2$ is N or D, and X$_3$ is F, I or L; and
  a CDR3 sequence of GSTSTAX$_4$PLRVDY (SEQ ID NO:3), where X$_4$ is T or K.

In the isolated or purified antibody fragment of the present invention, at least one of X$_1$, X$_2$, X$_3$, and X$_4$ is different from the corresponding wild type residues in CDR2 or CDR3 of FC5. More specifically, in an embodiment of the present invention, at least one of X$_1$, X$_2$, X$_3$ of CDR2 (SEQ ID NO: 2) and X$_4$ of CDR3 (SEQ ID NO: 3) is different from the corresponding wild type CDR2 and CDR3 sequences of SED ID NO:16, where the wild type CDR2 (SEQ ID NO:4) and CDR3 (SEQ ID NO: 10) correspond to residues 50-66 and 99-111 of SEQ ID NO: 16, respectively.

In certain embodiments of the isolated or purified antibody fragment of the present invention, the CDR2 is selected from the group consisting of RITWGGDNTFYSNSVKG (SEQ ID NO:4), RITWGGKNTFYSNSVKG (SEQ ID NO:5), RITWGGDDTFYSNSVKG (SEQ ID NO:6), RITWGGDNTIYSNSVKG (SEQ ID NO:7), and RITWGGDNTLYSNSVKG (SEQ ID NO:8), with the proviso that when CDR2 is RITWGGDNTFYSNSVKG (SEQ ID NO:4), CDR3 is not GSTSTATPLRVDY (SEQ ID NO:10).

In certain embodiments of the isolated or purified antibody fragment of the present invention, the CDR3 is GSTSTAKPLRVDY (SEQ ID NO:9) or GSTSTATPLRVDY (SEQ ID NO:10), with the proviso that when CDR3 is GSTSTATPLRVDY (SEQ ID NO:10), CDR2 is not RITWGGDNTFYSNSVKG (SEQ ID NO:4).

In a non-limiting example of the present invention, the isolated or purified antibody fragment may comprise:
  a CDR1 sequence of GFKITHYTMG (SEQ ID NO:1), a CDR2 sequence of RITWGGDNTFYSNSVKG (SEQ ID NO:4), and a CDR3 sequence of GSTSTAKPLRVDY (SEQ ID NO:9);
  a CDR1 sequence of GFKITHYTMG (SEQ ID NO:1), a CDR2 sequence of RITWGGKNTFYSNSVKG (SEQ ID NO:5), and a CDR3 sequence of GSTSTATPLRVDY (SEQ ID NO:10);
  a CDR1 sequence of GFKITHYTMG (SEQ ID NO:1), a CDR2 sequence of RITWGGDDTFYSNSVKG (SEQ ID NO:6), and a CDR3 sequence of GSTSTATPLRVDY (SEQ ID NO:10);
  a CDR1 sequence of GFKITHYTMG (SEQ ID NO:1), a CDR2 sequence of RITWGGDNTIYSNSVKG (SEQ ID NO:7), and a CDR3 sequence of GSTSTATPLRVDY (SEQ ID NO:10); or
  a CDR1 sequence of GFKITHYTMG (SEQ ID NO:1), a CDR2 sequence of RITWGGDNTLYSNSVKG (SEQ ID NO:8), and a CDR3 sequence of GSTSTATPLRVDY (SEQ ID NO:10).

In certain embodiments, the isolated or purified antibody fragment of the present invention comprises a sequence selected from the group consisting of:

```
                                          (SEQ ID NO: 11)
EVQLVESGGGLVQPGGSLRLSCAASGFKITHYTMGWFRQAPGKEREFVSR

ITWGGDNTFYSNSVKGRFTISRDNSKNTLYLQMNSLRAEDTAVYYCAAGS

TSTAKPLRVDYWGQGTLVTVSS;

(SEQ ID NO: 12)
EVQLVESGGGLVQPGGSLRLSCAASGFKITHYTMGWFRQAPGKEREFVSR

ITWGGKNTFYSNSVKGRFTISRDNSKNTLYLQMNSLRAEDTAVYYCAAGS

TSTATPLRVDYWGQGTLVTVSS;

(SEQ ID NO: 13)
EVQLVESGGGLVQPGGSLRLSCAASGFKITHYTMGWFRQAPGKEREFVSR

ITWGGDDTFYSNSVKGRFTISRDNSKNTLYLQMNSLRAEDTAVYYCAAGS

TSTATPLRVDYWGQGTLVTVSS;

(SEQ ID NO: 14)
EVQLVESGGGLVQPGGSLRLSCAASGFKITHYTMGWFRQAPGKEREFVSR

ITWGGDNTIYSNSVKGRFTISRDNSKNTLYLQMNSLRAEDTAVYYCAAGS

TSTATPLRVDYWGQGTLVTVSS;

(SEQ ID NO: 15)
EVQLVESGGGLVQPGGSLRLSCAASGFKITHYTMGWFRQAPGKEREFVSR

ITWGGDNTLYSNSVKGRFTISRDNSKNTLYLQMNSLRAEDTAVYYCAAGS

TSTATPLRVDYWGQGTLVTVSS;
``` and
  a sequence substantially identical thereto.

The isolated or purified antibody fragment of the present invention may be a single-domain antibody (sdAb). The sdAb may be humanized.

As described herein, the isolated or purified antibody fragment may be in a multivalent display format, using any suitable multimerizing technology. For example, the isolated or purified antibody fragment may be linked to a Fc fragment, thus forming a dimer. In this embodiment the Fc fragment may be any suitable Fc fragment, for example the mouse Fc2b or human Fc1, Fc2 or Fc4 sequences. In a specific example, the Fc may comprise the sequence of SEQ ID NO:29.

The isolated or purified antibody fragment of the present invention transmigrates the blood-brain barrier.

The present invention also encompasses a nucleic acid molecule encoding the isolated or purified antibody fragment as described herein. Vectors comprising the nucleic acid molecule encoding the isolated or purified antibody fragment are also included in the scope of the present invention.

The isolated or purified antibody fragment of the present invention may be immobilized onto a surface.

In another application, the isolated or purified antibody fragment as described above may be linked to a cargo molecule. Any suitable cargo molecule may be used. The cargo molecule may have a molecular weight in the range of about 1 kD to about 200 kDa. For example, and without wishing to be limiting, the cargo molecule may be a detectable agent, a therapeutic, a drug, a peptide, a growth factor, a cytokine, a receptor trap, a chemical compound, a carbohydrate moiety, an enzyme, a cargo antibody or antigen-binding fragment thereof such as an Fab or F(ab')$_2$, or cargo "antibody-like molecule" with antigen-binding activity, such as an scFv, a tandem di-scFv, a diabody, or a triabody, a DNA-based molecule, a viral vector, or a cytotoxic agent; one or more liposomes or nanocarriers loaded with a detectable agent, a therapeutic, a drug, a peptide, an enzyme, an antibody or fragment thereof, a DNA-based molecule, a viral vector, or a cytotoxic agent; or one or more nanoparticle, nanowire, nanotube, or quantum dots. In such a construct, the isolated or purified antibody fragment carries the cargo molecule across the blood-brain barrier.

In certain embodiments one antibody fragment is linked to the cargo molecule. In other embodiments two or more antibody fragments are linked to a cargo molecule. In such embodiments the antibody fragment may be linked to the cargo molecule directly, for example via a peptide bond, or the antibody fragment or fragments may be linked to the cargo molecule via a linker, such as peptide sequence of from 1 to 20 amino acids in length, or via different chemical linkers. A non-limiting example of a linker is a serine-glycine rich (S/G) linker of the sequence (GGGGS)n, where n may be 1, 2 or 3.

The present invention further encompasses a composition comprising one or more than one isolated or purified antibody fragment as described above and a pharmaceutically-acceptable carrier, diluent, or excipient.

The present invention encompasses humanized FC5 CDR mutants that show further 2-3-fold improvement of BBB crossing above that of FC5. Additionally, these antibody fragments show improved binding affinity to the brain endothelial receptor compared to FC5.

BRIEF DESCRIPTION OF THE DRAWINGS

These and other features of the invention will now be described by way of example, with reference to the appended drawings, wherein:

FIG. 7 shows the sequence alignment between the wild-type FC5 sequence (SEQ ID NO:16), humanized FC5 variant FC5-H7 (SEQ ID NO:17), and CDR mutants D56K (SEQ ID NO:12), N57D (SEQ ID NO:13), F59I (SEQ ID NO:14), F59 L (SEQ ID NO:15), and T105K (SEQ ID NO:11).

DETAILED DESCRIPTION OF THE INVENTION

Figure 1:
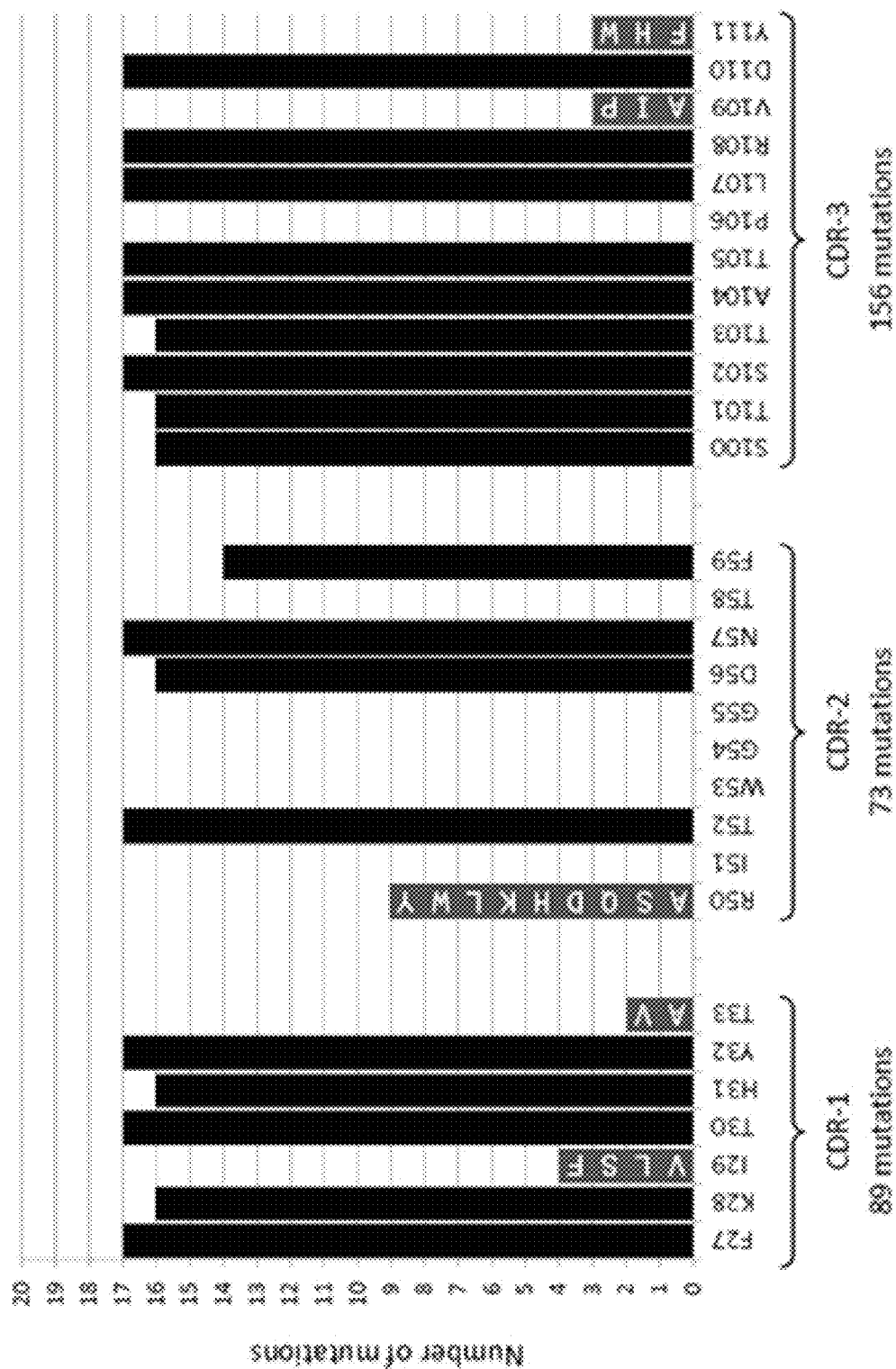
FIG. 1 shows the graphical representation of the distribution of 318 point mutations in CDR1, CDR2 and CDR3 of the FC5-H7. Black bars indicate full amino acid repertoire (except Cys and Met) at 18 positions. Slight variations are due to elimination of potential glycosylation sites. Gray bars indicate limited repertoires (labeled) at 5 positions.
Figure 2:
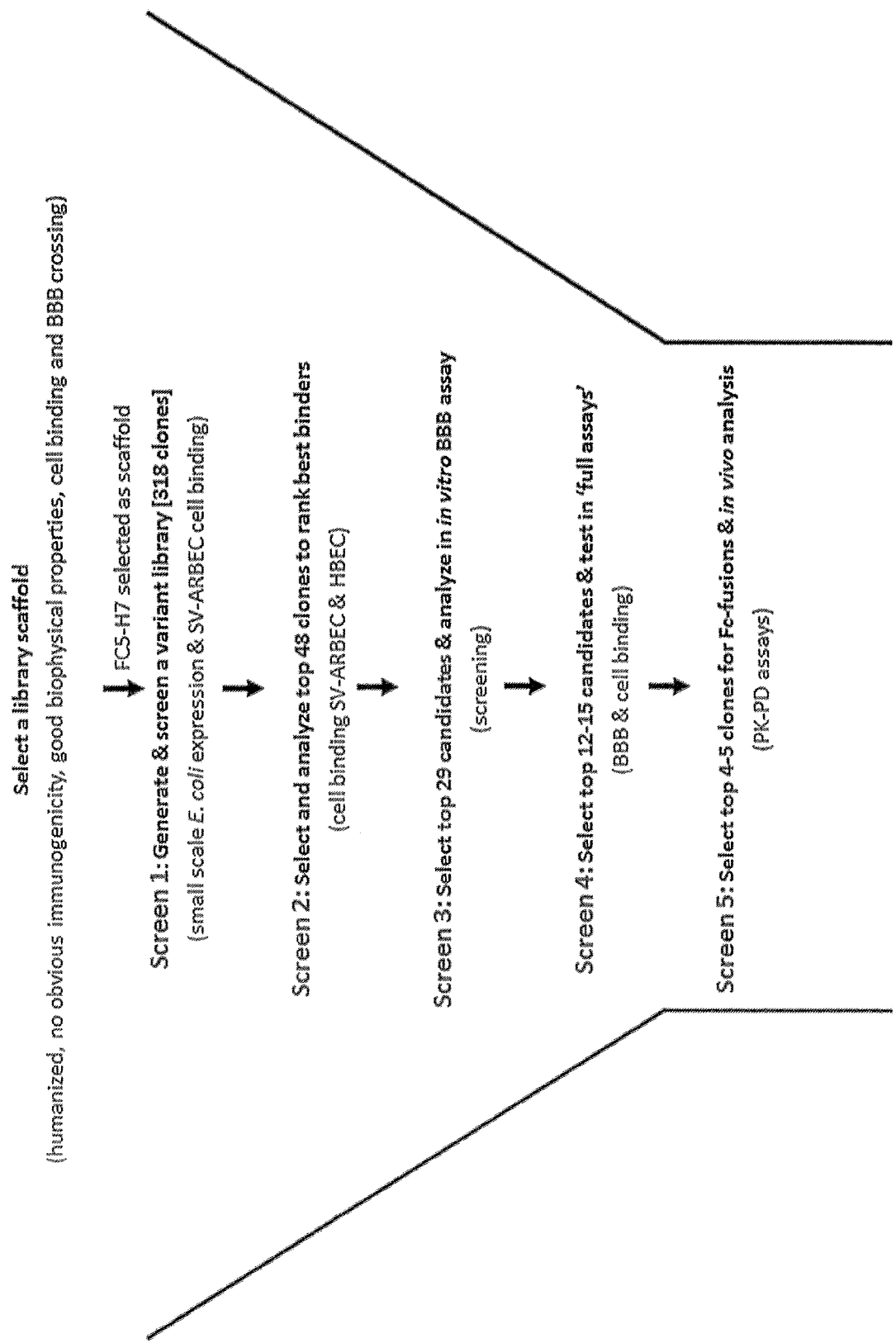
FIG. 2 shows a schematic of the selection strategy to choose affinity-improved clones from FC5-H7 mutational library.
Figure 3:
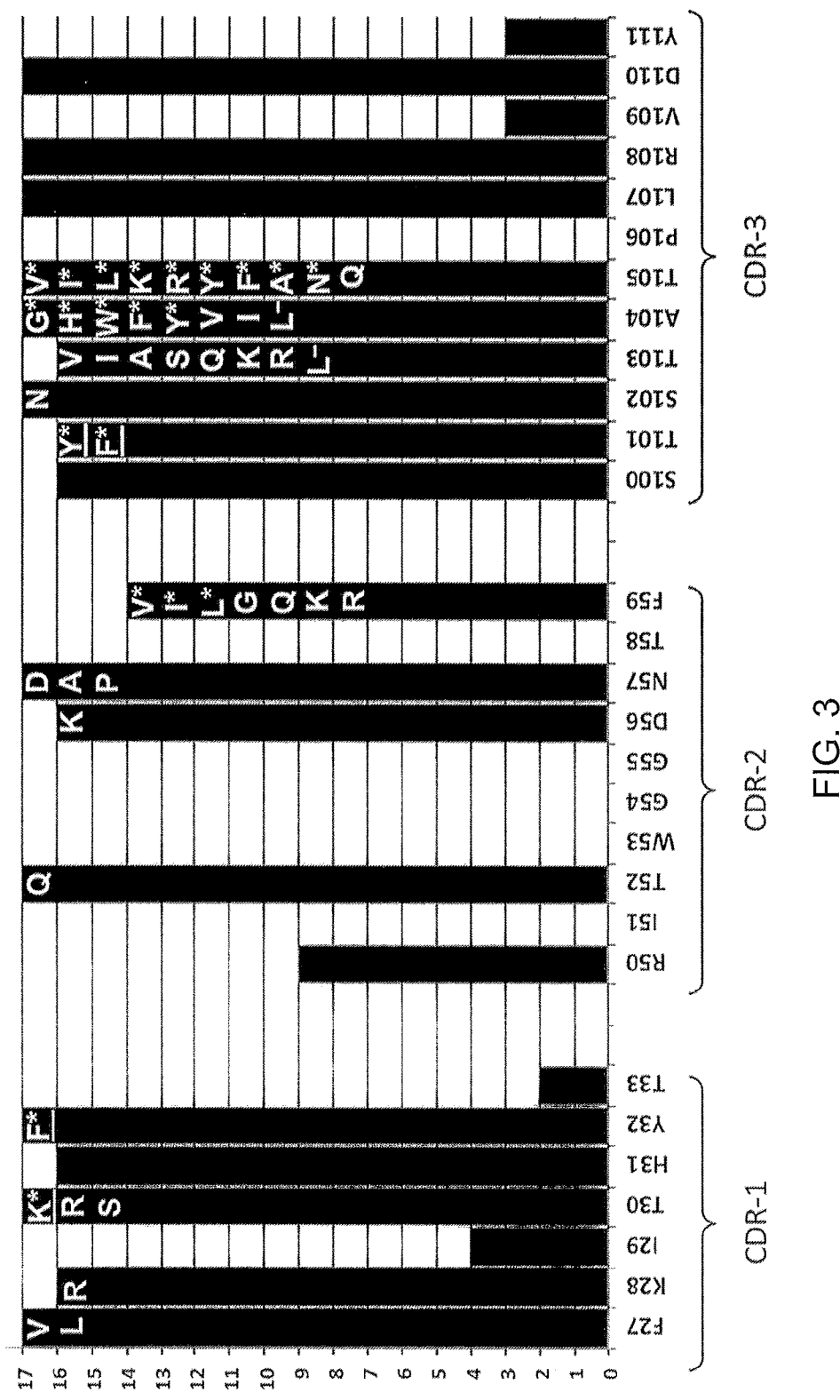
FIG. 3 shows graphical representation of the distribution of single point mutations in CDR1, CDR2 and CDR3 of FC5-H7 of 'top' 48 affinity improved variants selected in Screen 1 from FIG. 8. Affinity of 318 single-mutation variants was determined by a high-throughput binding assay to Simian virus 40-immortalized adult rat brain endothelial cells (SV-ARBEC) performed in Mirrorball instrument. White letters indicate moderate binders comparable with FC5-H7 (20 h binding); minus (−) signs indicate mutants exhibiting low binding (20 h binding, less than FC5-H7); asterisk (*) signs indicate strong binders (20 h binding); and underlined letters with asterisks indicate very strong binders (2 h binding).

The present invention relates to isolated or purified antibody fragments that transmigrate the blood-brain barrier, and uses thereof. More specifically, the present invention relates to antibody fragments derived by point-mutation of an existing antibody fragment and uses thereof; the antibody fragments of the present invention show enhanced transmigration across the blood-brain barrier.

The present invention provides an isolated or purified antibody fragment, comprising:
- a complementarity determining region (CDR) 1 sequence of GFKITHYTMG (SEQ ID NO:1);
- a CDR2 sequence of RITWGGX$_1$X$_2$TX$_3$YSNSVKG (SEQ ID NO:2), where X$_1$ is D or K, X$_2$ is N or D, and X$_3$ is F, I or L; and
- a CDR3 sequence of GSTSTAX$_4$PLRVDY (SEQ ID NO:3), where X$_4$ is T or K.

The antibody fragment of the present invention is a mutated version of the FC5 antibody described in WO 2002/057445. FC5 (SEQ ID NO:16) binds to the surface of mammalian brain endothelial cells and subsequently transmigrates the blood-brain barrier (BBB). FC5 has also been shown to act as a carrier to usher molecules of various sizes across the BBB (see for example, WO 2011/127580). Without wishing to be bound by theory, the antigen to which FC5 selectively binds and that mediates FC5 transmigration has been proposed to be transmembrane domain protein 30A (TMEM30A; WO 2007/036021), which is enriched on the surface of brain endothelial cells.

In the isolated or purified antibody fragment of the present invention, at least one of X$_1$, X$_2$, X$_3$, and X$_4$ is different from the corresponding wild type residues in CDR2 or CDR3 of FC5. More specifically, in an embodiment of the present invention, at least one of X$_1$, X$_2$, X$_3$ of CDR2 (SEQ ID NO: 2) and X$_4$ of CDR3 (SEQ ID NO: 3) is different from the corresponding wild type CDR2 and CDR3 sequences of SED ID NO:16, where the wild type CDR2 (SEQ ID NO:4) and CDR3 (SEQ ID NO: 10) correspond to residues 50-66 and 99-111 of SEQ ID NO: 16, respectively.

In antibody fragment described above, the CDR2 is selected from the group consisting of RIT-WGGDNTFYSNSVKG (SEQ ID NO:4), RIT-WGGKNTFYSNSVKG (SEQ ID NO:5), RIT-WGGDDTFYSNSVKG (SEQ ID NO:6), RITWGGDNTIYSNSVKG (SEQ ID NO:7), and RIT-WGGDNTLYSNSVKG (SEQ ID NO:8); whereas CDR3 may be selected from the group consisting of is GSTSTAK-PLRVDY (SEQ ID NO:9) or GSTSTATPLRVDY (SEQ ID NO:10), with the proviso that when CDR3 is GST-STATPLRVDY (SEQ ID NO:10), CDR2 is not RIT-WGGDNTFYSNSVKG (SEQ ID NO:4).

The term "antibody", also referred to in the art as "immunoglobulin" (Ig), generally refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable (V$_L$) and a constant (C$_L$) domain, while the heavy chain folds into a variable (V$_H$) and three constant (C$_H$, C$_{H2}$, C$_{H3}$) domains. Interaction of the heavy and light chain variable domains (V$_H$ and V$_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy (V$_H$) and light (V$_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the V$_H$ and V$_L$ domains. Chothia and Lesk (1987) define the "hypervariable loops" (H or L) based on the location of the structural loop regions in the V$_H$ and V$_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are identified herein according to the Kabat scheme.

An "antibody fragment" as referred to herein may include a single-domain antibody (sdAb; a fragment composed of a single V$_L$ or V$_H$) and multivalent presentations of sdAb. Antibody fragments such as those just described may require linker sequences, disulfide bonds, or other type of covalent bond to link different portions of the fragments; those of skill in the art will be familiar with the requirements of the different types of fragments and various approaches and various approaches for their construction.

The antibody fragment is derived from an sdAb from naturally-occurring or recombinant sources. Heavy chain antibodies of camelid origin (Hamers-Casterman et al, 1993) lack light chains and thus their antigen binding sites consist of one domain, termed $V_H H$. sdAb have also been observed in shark and are termed $V_{NAR}$ (Nuttall et al, 2003). Other sdAb may be engineered based on human Ig heavy or light chain sequences (Jespers et al, 2004; To et al, 2005). As used herein, the term "sdAb" includes those sdAb directly isolated from $V_H$, $V_H H$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb and transmigrate the BBB with improved ability over FC5.

SdAb possess desirable properties for antibody molecules, such as high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996). Further modifications to increase stability, such as the introduction of non-canonical disulfide bonds (Hussack et al, 2011; Kim et al, 2012), may also be brought to the sdAb.

A person of skill in the art would be well-acquainted with the structure of a single-domain antibody (see, for example, 3DVVT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3.

In one non-limiting example, the antibody fragment of the present invention may comprise:
a CDR1 sequence of GFKITHYTMG (SEQ ID NO:1), a CDR2 sequence of RITWGGDNTFYSNSVKG (SEQ ID NO:4), and a CDR3 sequence of GSTSTAKPLRVDY (SEQ ID NO:9);
a CDR1 sequence of GFKITHYTMG (SEQ ID NO:1), a CDR2 sequence of RITWGGKNTFYSNSVKG (SEQ ID NO:5), and a CDR3 sequence of GSTSTATPLRVDY (SEQ ID NO:10);
a CDR1 sequence of GFKITHYTMG (SEQ ID NO:1), a CDR2 sequence of RITWGGDDTFYSNSVKG (SEQ ID NO:6), and a CDR3 sequence of GSTSTATPLRVDY (SEQ ID NO:10);
a CDR1 sequence of GFKITHYTMG (SEQ ID NO:1), a CDR2 sequence of RITWGGDNTIYSNSVKG (SEQ ID NO:7), and a CDR3 sequence of GSTSTATPLRVDY (SEQ ID NO:10); or
a CDR1 sequence of GFKITHYTMG (SEQ ID NO:1), a CDR2 sequence of RITWGGDNTLYSNSVKG (SEQ ID NO:8), and a CDR3 sequence of GSTSTATPLRVDY (SEQ ID NO:10).

As previously stated, the antibody fragment may be an sdAb of camelid origin or derived from a camelid $V_H H$, and thus may be based on camelid framework regions. The present invention further encompasses an antibody fragment that is chimeric (or chimerized), veneered, or humanized. Chimeric antibody fragments encompass constructs in which the native variable domain (of camelid origin) is linked to human constant domain(s) (see Gonzales et al 2005). Veneering or re-surfacing of antibodies involves replacing exposed residues in the framework region of the native antibody fragment with the amino acid residues in their human counterpart (Padlan, 1991; Gonzales et al 2005). Humanization of an antibody comprises replacing an amino acid in the sequence with its human counterpart, as found in the human consensus sequence, without loss of antigen-binding ability or specificity; this approach reduces immunogenicity of the antibody fragment when introduced into human subjects. In this process, one or more than one of the CDR defined herein may be fused or grafted to a human variable region ($V_H$, or $V_L$), to other human antibody (IgA, IgD, IgE, IgG, and IgM), to human antibody fragment framework regions (Fv, scFv, Fab), or to human proteins of similar size and nature onto which CDR can be grafted (Nicaise et al, 2004). In such a case, the conformation of said one or more than one hypervariable loop is likely preserved, and the affinity and specificity of the sdAb for its target (i.e., brain endothelial cells) is likely minimally affected. As is known by those of skill in the art, it may be necessary to incorporate certain native amino acid residues into the human framework in order to retain binding and specificity. Humanization by CDR grafting is known in the art (for example, see Tsurushita et al, 2005; Jones et al, 1986; Tempest et al, 1991; Riechmann et al, 1988; Queen et al, 1989; reviewed in Gonzales et al, 2005—see also references cited therein), and thus persons of skill would be amply familiar with methods of preparing such humanized antibody or fragments thereof.

The CDR sequences as described above may be incorporated into a suitable antibody fragment scaffold. For example and without wishing to be limiting, the CDR sequences may be incorporated into the FC5 scaffold (SEQ ID NO:16); or into a humanized version of the FC5 scaffold as described in U.S. Provisional patent application No. 62/358,777 filed on Jul. 6, 2016, for example FC5-H7 (SEQ ID NO:17). The CDRs in the FC5 or humanized scaffolds correspond to residues 26-35 (CDR1), residues 50-66 (CDR2), and residues 99-111 (CDR3).

For example, and without wishing to be limiting in any manner, the isolated or purified antibody fragment as described above may be selected from the group consisting of:

```
                                        (SEQ ID NO: 11)
EVQLVESGGGLVQPGGSLRLSCAASGFKITHYTMGWFRQAPGKEREFVSR

ITWGGDNTFYSNSVKGRFTISRDNSKNTLYLQMNSLRAEDTAVYYCAAGS

TSTAKPLRVDYWGQGTLVTVSS;

(SEQ ID NO: 12)
EVQLVESGGGLVQPGGSLRLSCAASGFKITHYTMGWFRQAPGKEREFVSR

ITWGGKNTFYSNSVKGRFTISRDNSKNTLYLQMNSLRAEDTAVYYCAAGS

TSTATPLRVDYWGQGTLVTVSS;
```

```
                                                (SEQ ID NO: 13)
EVQLVESGGGLVQPGGSLRLSCAASGFKITHYTMGWFRQAPGKEREFVSR

ITWGGDDTFYSNSVKGRFTISRDNSKNTLYLQMNSLRAEDTAVYYCAAGS

TSTATPLRVDYWGQGTLVTVSS;

(SEQ ID NO: 14)
EVQLVESGGGLVQPGGSLRLSCAASGFKITHYTMGWFRQAPGKEREFVSR

ITWGGDNTIYSNSVKGRFTISRDNSKNTLYLQMNSLRAEDTAVYYCAAGS

TSTATPLRVDYWGQGTLVTVSS;

(SEQ ID NO: 15)
EVQLVESGGGLVQPGGSLRLSCAASGFKITHYTMGWFRQAPGKEREFVSR

ITWGGDNTLYSNSVKGRFTISRDNSKNTLYLQMNSLRAEDTAVYYCAAGS

TSTATPLRVDYWGQGTLVTVSS;
```
and
a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides.

In a non-limiting example, a conservative mutation may be a conservative amino acid substitution. A conservative amino acid substitution is defined herein as the substitution of an amino acid residue for another amino acid residue with similar chemical properties (e.g. size, charge, or polarity). These conservative amino acid mutations are made to the framework regions of the sdAb while maintaining the CDR sequences listed above and the overall structure of the CDR of the antibody fragment; thus the specificity and binding of the antibody are maintained. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. This corresponds to 1, 2, 3, 4, 5, 6, 7, 8, 9, 10, 11, or 12 conservative amino acid mutations. Importantly, the substantially identical sequences retain the activity and specificity of the reference sequence (that is, the ability to transmigrate the BBB). In a non-limiting embodiment, the difference in sequence identity may be due to conservative amino acid mutation(s). In a non-limiting example, the present invention may be directed to an antibody fragment comprising a sequence at least 95% (corresponding to 6 conservative amino acid mutations), 98% (corresponding to 2 conservative amino acid mutations), or 99% (corresponding to 1 conservative amino acid mutation) identical to that of the antibodies described herein. It is additionally understood that calculating a percentage sequence identity involves a comparison with the complete sequence of the antibody fragment.

The antibody fragment of the present invention may also comprise additional sequences to aid in expression, detection or purification of a recombinant antibody or fragment thereof. Any such sequences or tags known to those of skill in the art may be used. For example, and without wishing to be limiting, the antibody fragment may comprise a targeting or signal sequence (for example, but not limited to ompA), a detection/purification tag (for example, but not limited to c-Myc, $His_5$, or $His_6$), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody fragment of the present invention may also be in a multivalent display format, also referred to herein as multivalent presentation. Multimerization may be achieved by any suitable method of known in the art. For example, and without wishing to be limiting in any manner, multimerization may be achieved using self-assembly molecules such as those described in WO2003/046560, where pentabodies are produced by expressing a fusion protein comprising an antibody fragment and the pentamerization domain of the B-subunit of an $AB_5$ toxin family (Merritt & Hol, 1995). A multimer may also be formed using the multimerization domains described by Zhu et al. (2010); this form, referred to herein as a "combody" form, is a fusion of the antibody fragment with a coiled-coil peptide resulting in a multimeric molecule. Other forms of multivalent display are also encompassed by the present invention. For example, and without wishing to be limiting, the antibody fragment may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996).

Another method known in the art for multimerization is to dimerize the antibody fragment using an Fc domain, for example, but not limited to, human Fc domains. The Fc domains may be selected from various classes including, but not limited to, IgG, IgM, or various subclasses including, but not limited to IgG1, IgG2, IgG3, and IgG4. In this approach, the Fc encoding polynucleotide is inserted into a vector along with the sdAb encoding polynucleotide to generate a sdAb-Fc fusion protein (Bell et al, 2010; Iqbal et al, 2010); the fusion protein is recombinantly expressed then purified. For example, and without wishing to be limiting in any manner, multivalent display formats may encompass chimeric formats of FC5-H7 mutational variants linked to an Fc domain. Such chimeric format molecules are readily engineered and produced, can greatly extend the serum half-life of sdAb, and may be excellent tumor imaging reagents (Bell et al., 2010).

The Fc domain in the multimeric complex as just described may be any suitable Fc fragment known in the art. The Fc fragment may be from any suitable source; for example, the Fc may be of mouse or human origin. In a specific, non-limiting example, the Fc may be the mouse IgG2b Fc fragment or human IgG1, IgG2 or IgG4 Fc fragment (Bell et al, 2010; Iqbal et al, 2010). In a specific, non-limiting example, the multimerized construct may comprise the isolated or purified antibody fragment as described herein and an Fc comprising the sequence of SEQ ID NO:29.

Each subunit of the multimers described above may comprise the same or different antibody fragments of the present invention, which may have the same or different specificity. Additionally, the multimerization domains may be linked to the antibody fragment using a linker, as required; such a linker should be of sufficient length and appropriate composition to provide flexible attachment of the two molecules, but should not hamper the antigen-binding properties of the antibody.

The antibody fragment as described herein transmigrates the blood-brain barrier. The brain is separated from the rest of the body by a specialized endothelial tissue known as the blood-brain barrier (BBB). The endothelial cells of the BBB are connected by tight junctions and efficiently prevent many therapeutic compounds from entering the brain. In addition to low rates of vesicular transport, one specific feature of the BBB is the existence of enzymatic barrier(s) and high level(s) of expression of ATP-dependent transporters on the abluminal (brain) side of the BBB, including P-glycoprotein (Gottesman et al., 1993; Watanabe, 1995), which actively transport various molecules from the brain into the blood stream (Samuels, 1993). Only small (<500 Daltons) and hydrophobic (Pardridge, 1995) molecules can more readily cross the BBB. Thus, the ability of the antibody fragment as described above to specifically bind the surface receptor, internalize into brain endothelial cells, and undergo transcytosis across the BBB by evading lysosomal degradation is useful in the neurological field.

The present invention also encompasses nucleic acid sequences encoding the molecules as described herein. Given the degeneracy of the genetic code, a number of nucleotide sequences would have the effect of encoding the polypeptide, as would be readily understood by a skilled artisan. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody fragments immobilized onto a surface using various methodologies; for example, and without wishing to be limiting, the antibody fragment may be linked or coupled to the surface via His-tag coupling, biotin binding, covalent binding, adsorption, and the like. Immobilization of the antibody fragment of the present invention may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, or any other useful surface such as nanoparticles, nanowires and cantilever surfaces.

The invention also encompasses one or more antibody fragments as described above linked to a cargo molecule. The cargo molecule may be any suitable molecule, which is delivered across the BBB by the antibody fragment. The cargo molecule may have a molecular weight in the range of about 1 kD to about 200 kDa; for example, the cargo molecule may have a molecular weight of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kDa, or any weight therebetween, or any range of weights defined by any two aforementioned weights. In specific, non-limiting examples, the cargo molecule may have a molecular weight of about 80 kDa (for example, but not limited to a Fc fragment, toxin, growth factor, cytokine, enzyme, protein, antibody, single-domain antibody, or antibody fragment, etc), or about 200 kDa (for example, but not limited to a monoclonal antibody).

For example, and without wishing to be limiting in any manner, the cargo molecule may be a detectable agent, a therapeutic agent, a drug, a peptide, an enzyme, a growth factor, a cytokine, a receptor trap, a cargo antibody or a fragment of a cargo antibody (e.g., IgG, scFv, Fab, F(ab)$_2$, V$_H$H, etc) a chemical compound, a carbohydrate moiety, DNA-based molecules (anti-sense oligonucleotide, microRNA, siRNA, plasmid), a cytotoxic agent, viral vector (adeno-, lenti-, retro), one or more liposomes loaded with any of the previously recited types of cargo molecules, or one or more nanoparticle, nanowire, nanotube, or quantum dots. The cargo molecule as described above may be a detectable agent. For example, the FC5 antibody variant fragment may be linked to a radioisotope, a paramagnetic label, a fluorophore, a fluorescent agent, Near Infra-Red (NIR; for example Cy5.5) fluorochrome or dye, an echogenic microbubble, an affinity label, a detectable protein-based molecule, nucleotide, quantum dot, nanoparticle, nanowire, or nanotube or any other suitable agent that may be detected by imaging methods. The antibody fragment may be linked to the cargo molecule using any method known in the art (recombinant technology, chemical conjugation, etc.).

The cargo molecule as described herein may be linked, also referred to herein as "conjugated", to the antibody fragment by any suitable method known in the art. For example, and without wishing to be limiting, the cargo molecule may be linked to the antibody fragment by a covalent bond, by a peptide bond, or by ionic interaction. For example, and without wishing to be limiting, the antibody fragment linked to a cargo molecule may be expressed as a fusion protein. The linkage may be achieved through a chemical cross-linking reaction, or through fusion using recombinant DNA methodology combined with any peptide expression system, such as bacteria, yeast or mammalian cell-based systems. When conjugating the cargo molecule to the antibody fragment, a suitable linker may be used. Methods for linking an antibody fragment to a cargo molecule such as a therapeutic or detectable agent would be well-known to a person of skill in the art.

In one non-limiting example, the cargo molecule may be a detectable label, a radioisotope, a paramagnetic label such as gadolinium or iron oxide, a fluorophore, Near Infra-Red (NIR) fluorochrome or dye, an echogenic microbubble, an affinity label (for example biotin, avidin, etc), enzymes, or any other suitable agent that may be detected by diagnostic imaging methods. In a specific, non-limiting example, the antibody fragment may be linked to a near infrared fluorescence (NIRF) imaging dye, for example and not wishing to be limiting Cy5.5, Alexa680, Dylight680, or Dylight800.

The in vivo detection step in the methods described above may be whole body imaging for diagnostic purposes or local imaging at specific sites, such as but not limited to brain vessels or brain tumor vessels, in a quantitative manner to assess the progression of disease or host response to a treatment regimen. The detection step in the methods as described above may be immunohistochemistry, or a non-invasive (molecular) diagnostic imaging technology including, but not limited to:

- Optical imaging;
- Positron emission tomography (PET), wherein the detectable agent is an isotopes such as $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, with $^{18}F$ being the most clinically utilized;
- Single photon emission computed tomography (SPECT), wherein the detectable agent is a radiotracer such as $^{99m}Tc$, $^{111}In$, $^{123}I$, $^{201}Tl$, $^{133}Xe$, depending on the specific application;
- Magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques.
- Contrast-Enhanced Ultrasonography (CEUS) or ultrasound, wherein the detectable agent is at least one acoustically active and gas-filled microbubble. Ultrasound is a widespread technology for the screening and early detection of human diseases. It is less expensive than MRI or scintigraphy and safer than molecular imaging modalities such as radionuclide imaging because it does not involve radiation.

The present invention further provides a method of transporting a molecule of interest across the blood-brain barrier. The method comprises administering the molecule linked to an antibody fragment as described herein to a subject. The molecule may be any desired molecule, including the cargo molecules, as previously described; the molecule may be "linked" to the antibody fragment using any suitable method, including, but not limited to conjugation or expression in a fusion protein. The administration may be by any suitable method, for example parenteral administration, including but not limited to intravenous (iv), subcutaneous (sc), and intramuscular (im) administration. In this method, the antibody fragment of the present invention 'ferries' the molecule of interest across the BBB to its brain target.

The present invention also encompasses a composition comprising one or more than one isolated or purified antibody fragment as described herein. The composition may comprise a single antibody fragment as described above, or may be a mixture of antibody fragments. Furthermore, in a composition comprising a mixture of antibody fragments of the present invention, the antibodies may have the same specificity, or may differ in their specificities;

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but not necessarily limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody fragment. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody fragment to the gastrointestinal tract of the subject. Thus, the composition may comprise encapsulation, time-release, or other suitable technologies for delivery of the antibody fragment. It would be within the competency of a person of skill in the art to prepare suitable compositions comprising the present compounds.

Typically, only a small fraction (<0.01%) of injected antibody or antibody fragment dose crosses the BBB. The FC5 $V_HH$ (WO 2002/057445) was previously identified for its ability to transmigrate the BBB. Various antibody or protein fusion constructs with FC5 have shown 10-15 fold improvement of brain uptake compared to control antibody without an FC5 component. The present inventors have now identified specific mutations within the complementarity-determining regions of FC5 that lead to improved binding of the antibody to brain endothelial cells. Specifically, mutants D56K, N57D, F59I, F59L, and T105K demonstrated improved binding in both SV-ARBEC and HBEC. The same mutants showed improvements in the range of 33-448% increase in $P_{app}$ values compared to FC5-H7 (a humanized FC5), indicating improvement in their rate of transport across the in vitro BBB model. When fused to a Fc, most mutants maintained improved binding to SV-ARBEC compared to FC5-Fc and showed higher $P_{app}$ values compared to FC5-H7-Fc fusion. The results suggest that specific mutations introduced into CDRs resulted in both the improvement in affinity and in enhanced BBB crossing in vitro. Furthermore, selected mutants tested for delivery of the antibody fragments to the brain showed 1.5 to 3-fold increase in brain levels, demonstrating better brain penetration and higher brain levels compared to the FC5-H7-Fc construct.

The present invention will be further illustrated in the following examples. However, it is to be understood that these examples are for illustrative purposes only and should not be used to limit the scope of the present invention in any manner.

Example 1: Design of CDR Mutation Library

Based on the sequence of FC5 (SEQ ID NO:16), single point-mutations within the antibody's CDR were designed to improve performance. The modeled 3D-structure of the CDR conformation of FC5 was used to inform the construction of the sdAb mutants.

3D-Structure Modeling of Camelid V$_H$H.

Template structures similar to FC5 V$_H$H were identified using BLAST searches against the Protein Data Bank (PDB). The 3D structure of the FC5 V$_H$H was approximated using homology modeling based on the 2X1O|A (PDB code|Chain ID) structure as template. The FC5 V$_H$H structure was then built by mutating the template structure to the FC5 sequence; this included 32 mutations at various positions (26 in the CDR and 6 in the framework region). The FC5 V$_H$H model was then refined by energy minimization with the AMBER force-field and a stepwise release of constraints, ranging from the CDR loops, which were relaxed first, to the backbone heavy atoms of the framework region, which were fully relaxed only in the last stage. The CDR-H3 loop of the V$_H$H model was then refined by Monte-Carlo-minimization (MCM) conformational sampling, in which dihedral angles in the CDR-H3 region were sampled followed by energy minimization.

The selected humanized framework for this work was that of FC5-H7 (SEQ ID NO:17), which demonstrated an optimal balance of low predicted immunogenicity, high production yield, and elevated thermal stability. Humanized FC5-H7 was constructed and produced as described in PCT application PCT/IB2017/054036, the contents of which are incorporated herein by reference.

The FC5 CDR contain 29 residues: 7 in CDR1 (residues 26-35, SEQ ID NO:16), 10 in CDR2 (residues 50-66, SEQ ID NO:16) and 12 in CDR3 (residues 99-111, SEQ ID NO:16). Mutations were focused on solvent-accessible residues that did not appear to play a structural role in the CDR. The following mutations were selected for introducing into the FC5-H7: D56K, N57D, F59I, F59L, and T105K.

Example 2: Library Construction and Plasmid Production

The single point-mutations identified in Example 1 were introduced into the FC5-H7 sequence.

To generate the cDNA sequences for the single-point mutants, the respective preferred E. coli codon was used for the point mutant and embedded within the cDNA sequence of the FC5-H7. All variants were expressed in fusion with His5 and c-myc tags to allow for purification by immobilized metal affinity chromatography using HiTrap Chelating™ column and for detection by immunochemistry, respectively.

Briefly, DNA encoding sdAb FC5-H7 (SEQ ID NO:17) or point-mutants was cloned into the BbsI/BamHI sites of plasmid pSJF2H to generate expression vector for FC5 (Muruganandam et al, 2002). The DNA constructs were confirmed by nucleotide sequencing on 373A DNA Sequencer Stretch (PE Applied Biosystems) using primers fdTGIII, 5'-GTGAAAAAATTATTATTATTCGCAAT-TCCT-3' (SEQ ID NO:18) and 96GIII, 5'-CCCTCATAGT-TAGCGTAACG-3' (SEQ ID NO:19).

Example 3: Very Small Scale Expression and Purification of 318 FC5-H7 CDR Mutants The plasmids produced in Example 2 were cloned into E. coli cells, expressed, and purified on a small scale to assess the performance of each clone.

Protein Expression:

The CDR-mutated variants were synthesized and directly cloned into pSJF2H as described in Example 2. Subsequently, 50 ng of DNA was transformed into 5 µl of Zymo Research Mix and Go electro-competent TG1 E. coli. (Cedarlane) for 10 min at 4° C. then 100 µl of 2YT media was added (tryptone 16 g, yeast extract 10 g and NaCl 5 g in 1 L). Clones were selected on 6 well 2YT agar plates+100 µg/ml ampicillin and grown overnight at 32° C. followed by 3-4 hours of growth at 37° C. Cultures were inoculated into 5 ml of 2YT/glu/amp (2YT media supplemented with 100 µg/ml ampicillin and 0.1% glucose) and grown at 37° C., 250 rpm in Kingfisher 24 well deep plates. Protein expression was induced at an OD$_{600}$ of 0.4-0.5 with addition of IPTG to a final concentration of 1 mM. The cultures were grown at 250 rpm overnight at 37° C. The bacteria were pelleted by plate centrifugation, 3000 rpm for 15 min. The supernatant was discarded and the pellets were frozen at −80° C. for 20 min. The partially thawed pellets were re-suspended in 1 ml of lysis buffer (1×PBS supplemented with 0.1 M Hepes pH 7.5, 10 ml of FastBreak (Fisher), 1×EDTA protease inhibitor tablet (Roche), 200 µl of DNase (Sigma), in 100 ml) and lysed for 30 min at 250 rpm. The plates were centrifuged at 3000 rpm for 15 min and the supernatant was transferred into new 24 well deep plates for Kingfisher purification. Pure Proteome nickel magnetic beads (Millipore) were centrifuged at 400×g for 1 min then washed in 40 ml of buffer A (500 mM NaCl; 10 mM Hepes pH 7.5) centrifuged again then re-suspended in a final volume of 10 ml. A 200 µl volume of prepared beads was added to the Kingfisher 24 well deep plates containing the expressed c-myc/His-dual tagged V$_H$H single domain antibody variants and incubated for 30 min at 270 rpm.

KingFisher™ Flex Magnetic Particle Processor Purification:

A washing buffer plate (500 mM NaCl, 10 mM Hepes pH7.5 and 10 mM imidazole, 2 ml/well), an elution buffer plate (500 mM NaCl, 10 mM Hepes pH 7.5 and 300 mM imidazole, 300 µl/well), a collection buffer plate (50 mM EDTA, 0.5 ml/well), a 24 well tip comb (VWR), and the Kingfisher 24 well deep plates containing the c-myc/His-dual tagged V$_H$H single domain antibody/nickel magnetic beads were inserted into the KingFisher™ Flex Magnetic Particle Processor. The purification protocol (Hiba_KF optimized) was initiated with the following steps: collection of beads from sample plate—wash 1 min at medium speed—bead collection—elution by mixing 5 min at medium speed—bead collection—release of beads into EDTA and drive home. EDTA at a 2 mM final concentration was added to each protein elution plate prior to storage at 4° C. In preparation for cell binding analysis and affinity ranking by Mirrorball® High Sensitivity Microplate Cytometry the samples were transferred to 96-well Sephadex G-25 desalting plates (GE Healthcare) to remove the imidazole and to buffer exchange the purified V$_H$H single domain antibodies into 250 µl PBS+EDTA 0.5 mM. Protein purity was assessed by Mini-Protein TGX 4-20% stain free SDS-Page gels and band visualization with a Bio-Rad Gel Dock™ EZ System. Protein concentration was measured by Nanodrop.

Example 4. Initial Selection for Affinity-Improved FC5 Variants

The selection strategy for the FC5 mutants was based on screening of all variants expressed in small quantity using Mirrorball® binding assay (see below). The first screening round is performed in rat brain endothelial cells SV-AR-BEC. The clones with best binding affinity to SV-ARBEC were then re-tested for binding in both SV-ARBEC and human brain endothelial cells (HBEC) using the same binding assay.

Mirrorball® High Sensitivity Microplate Cytometry (TTP Labtech):

All buffers and reagents were pre-chilled to 4° C. Each sdAb mutant was diluted to a starting concentration of 1000 nM in a 1:1 buffer mix of 0.5×PBS/2.5 mM EDTA and Mirrorball assay buffer—Live Cell Imaging Solution, LCIB (Invitrogen, 140 mM NaCl, 2.5 mM KCl, 1.8 mM $CaCl_2$, 1.0 mM $MgCl_2$, 20 mM Hepes, pH 7.4, mOsm=300). A 20 µl volume of a 1:1 mix of LCIB and 0.5×PBS/2.5 mM EDTA was added to all wells of each 384 well Mirrorball assay plate (Corning 3712); with the exception of row A which received 40 µl of 1000 nM test $V_HH$ antibody. Serial dilutions were prepared for each test variant within the Mirrorball 384 well assay plate. A 16-channel Finn pipette (Thermo Scientific) was used to transfer 20 µl of $V_HH$ antibody from row A-columns 1-24 into row B-columns 1-24 mixing 8×, then transferring 20 µl of $V_HH$ antibody from row B-columns 1-24 into row C-columns 1-24 mixing 8×. Dilutions were repeated until row G-columns 1-24 to create 7 point curve for each mutant. A second set of test $V_HH$ antibody variants (1000 nM) were added to row I-columns 1-24 and the dilution protocol was repeated until row O-columns 1-24. Row H-columns 1-24 were reserved on each plate for the reference FC5-H7 $V_HH$ single domain antibody. Row P-columns 1-24 received no antibody; this was background control for non-specific binding of the secondary to the cells of interest; thus 48 variants could be tested on each 384 well Mirrorball assay plate. Immortalized adult rat brain microvascular endothelial cells (SV-ARBEC) and/or human microvascular brain endothelial cells (HBEC-D3) were dissociated in Accutase solution (Sigma Aldrich) to generate single cell populations. Cells were washed in LCIB then centrifuged at 200×g, 5 min to pellet. Wash buffer was removed and the cell pellet was re-suspended into 1 mL of LCIB. Cell number was calculated using a Bio-Rad TC20 automated cell counter with Trypan Blue dye to assess viability. The cells were diluted to 350,000 live cells/ml in LCIB. A fluorescent conjugate c-myc Alexa 488 detection antibody (1600 ng/ml, Santa Cruz Biotechnology) supplemented with Draq 5 nuclear stain (2 uM, Cell Signaling) was prepared in LCIB assay buffer. The cells and the detection secondary/Drag 5 solution were mixed 1:1 and 20 µl of solution containing 3500 cells was added into each well of the Mirrorball 384 well assay plate; which already contained each $V_HH$ antibody variant in a 7 point dilution series resulting in a final concentration of 500, 250, 125, 62.5, 31.25, 15.63 and 7.81 nM. All plates were incubated at 4° C. for 2 h and 20 h. Readings were taken at each time point using Mirrorball High Sensitivity Microplate Cytometry with the following settings:

Laser Settings: 488 and 640 enabled, 6.0 mW

Channel Settings: FL-2 (488-540 nm) voltage 600, sensitivity 4, Tiff files saved and FL-4 (650-690 nm) voltage 600, sensitivity 4, trigger 4, Tiff files saved Object Characteristics: FL-2 (peak intensity, mean intensity, total intensity, and baseline) and FL-4 (peak intensity, mean intensity, total intensity and baseline)

Population Definition: Objects—Cells Filters (FL-4 perimeter range 0-500 nm and FL-2 mean intensity range 0-15000)

Population Statistics: Objects: number of objects, Objects: mean (FL-2 peak, mean, total intensities and perimeter) and Objects: mean FL-2 baseline. Objects: median (FL-2 peak, mean, and total intensities) Objects: mean (FL-4 peak, mean, total intensities and perimeter) and Objects: mean FL-4 baseline. Objects: median (FL-4 peak, mean, and total intensities) Cells: number of objects, Cells: mean (FL-2 peak, mean, and total intensities) and Cells: mean FL-2 baseline. Cells: median (FL-2 peak, mean, and total intensities) Cells: mean (FL-4 peak, mean, and total intensities) and Cells: mean FL-4 baseline. Cells: median (FL-4 peak, mean, and total intensities)

The remaining live cell material was incubated at 4° C. adjacent to the assay plate so cell viability could be monitored at both 2 h and 20 h time points. The Mirrorball assay procedure was repeated for all $V_HH$ single domain antibodies until all 318 variants were screened in both SV-ARBEC and HBEC-D3 cell lines of interest. The data was analysed with Cellista software (TTP Labtech) and GraphPad Prism 6 software programs.

Figure 4B:
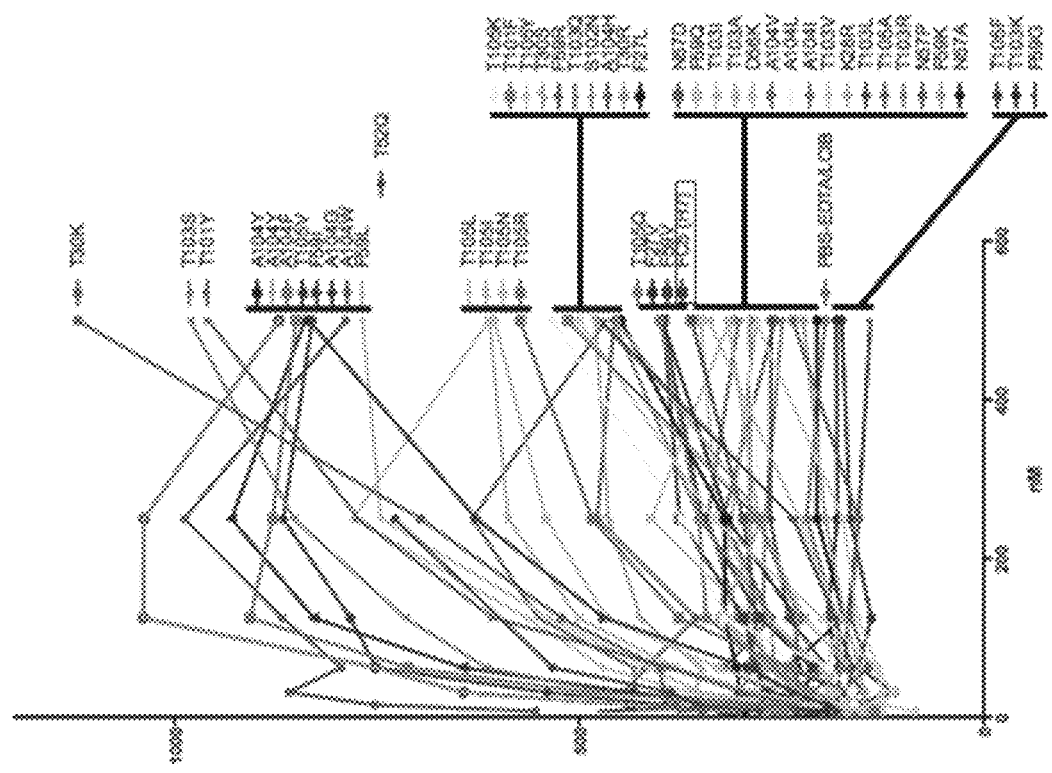
FIG. 4 shows ranking of the 48 single-mutation variants of FC5-H7 shown in FIG. 3 in binding assays using rat SV-ARBEC (FIG. 4A) and human brain endothelial cell (HBEC)-D3 (FIG. 4B) cell lines. Binding curves were generated with serial dilutions of each antibody using a fluorescent conjugate c-myc Alexa 488 detection antibody (1600 ng/ml, Santa Cruz Biotechnology) supplemented with Draq 5 nuclear stain (2 uM, Cell Signaling) for detection of cell-bound antibody. All plates were incubated at 4° C. for 2 h and 20 h. Readings were taken at each time point using Mirrorball High Sensitivity Microplate Cytometry as described below.
Figure 4A:
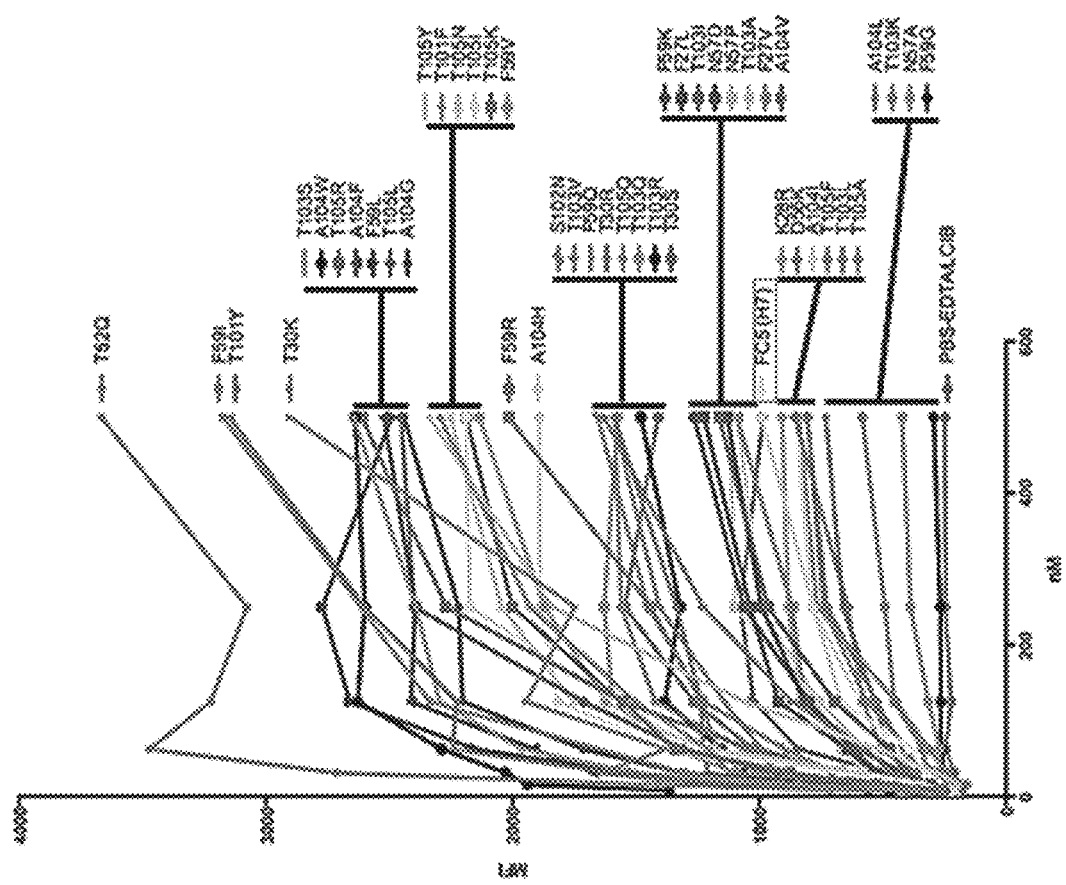
Figure 5:
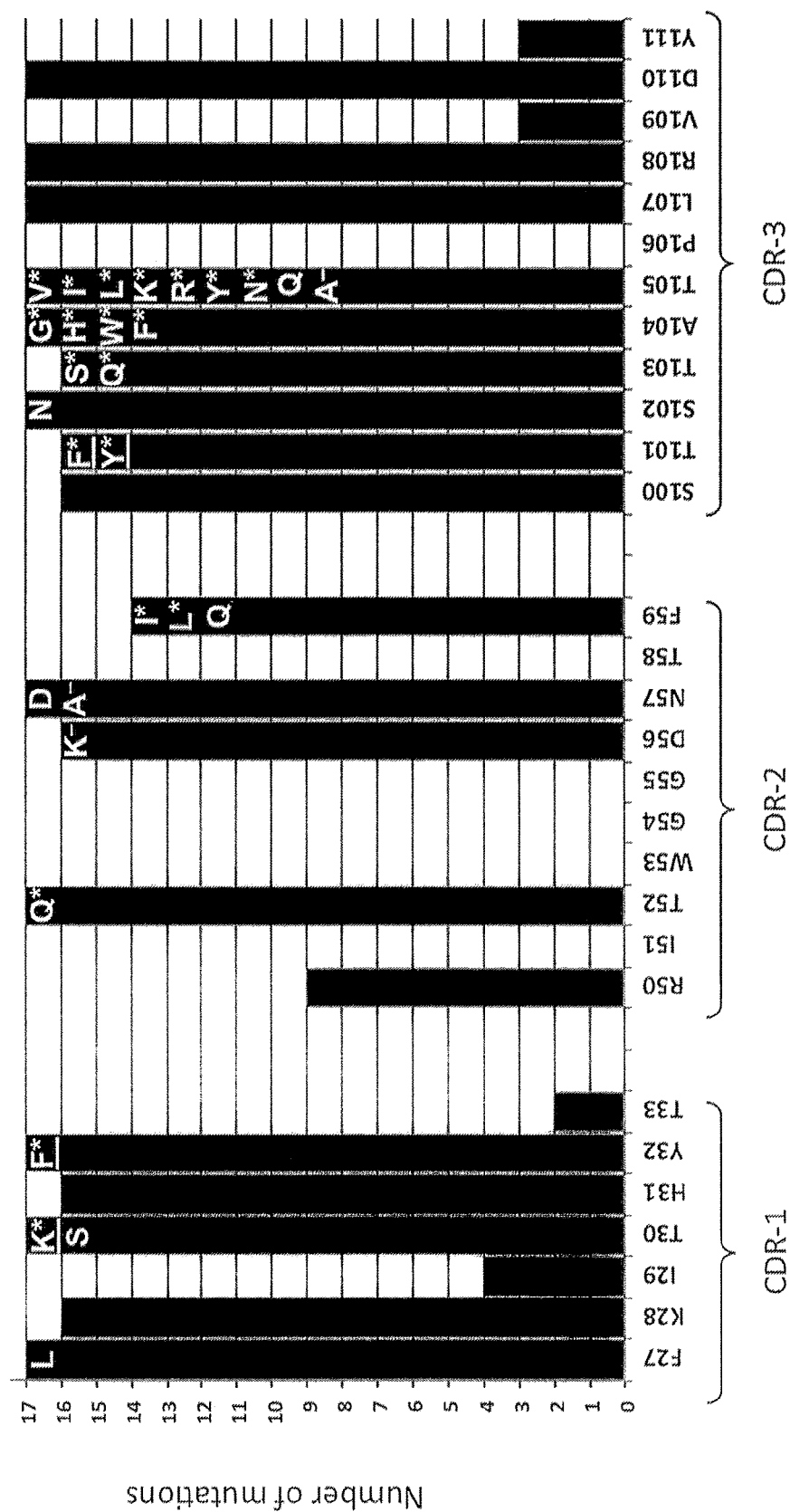
FIG. 5 shows graphical representation of the distribution of single point mutations in CDR1, CDR2 and CDR3 of FC5-H7 of 'top' 29 affinity improved variants show in FIG. 4 selected in Screen 2 shown in FIG. 2. White letters indicate moderate affinities similar to FC5-H7; minus (−) signs indicate mutants exhibiting lower affinities than FC5-H7; asterisk (*) signs indicate higher affinities than FC5-H7; and underlined letters with asterisks indicate significantly higher affinities than FC5-H7.

Some clones showed no binding or lower binding to SV-ARBEC compared to FC5. The clones showing improved binding were selected for further studies in both SV-ARBEC and HBEC cells, as described above. FIG. 4 shows the binding curves of the 48 clones in SV-ARBEC and HBEC cells.

Example 5: Transport of FC5-H7 CDR Variants Across In Vitro BBB Model

The top candidates of the 48 clones identified in Example 4 demonstrating improved binding in both SV-ARBEC and HBEC cells were screened in in vitro BBB permeability assay, using a single-time point for Papp determination. The quantification of variants was done using by MRM-ILIS.

SV40-immortalized Adult Rat Brain Endothelial Cells (SV-ARBEC) were used to generate an in vitro blood-brain barrier (BBB) model as described (Garberg et al., 2005; Haqqani et al., 2012). Sv-ARBEC (80,000 cells/membrane) were seeded on a 0.1 mg/mL rat tail collagen type I-coated tissue culture inserts (pore size-1 µm; surface area 0.9 $cm^2$, Falcon) in 1 ml of growth medium. The bottom chamber of the insert assembly contained 2 ml of growth medium supplemented with the immortalized neonatal rat astrocytes-conditioned medium in a 1:1 (v/v) ratio. Equimolar amounts (5.6 µM) of positive (FC5) or negative controls (A20.1, a *Clostridium difficile* toxin A binding $V_HH$; and EG2, an EGFR binding $V_HH$), FC5, FC5-H7 and 29 point-mutants from Example 4 were tested for their ability to cross the rat in vitro BBB model. Following exposure of equimolar amounts of the sdAb to the luminal side of the BBB, samples were taken after 15, 30 and 60 min from the abluminal side. The sdAb content of each sample was then quantified by mass spectrometry (multiple reaction monitoring-isotype labeled internal standards; MRM-ILIS).

MRM-ILIS:

The methods are all as described in Haqqani et al. (2012). Briefly, to develop the SRM (selected reaction monitoring also known as multiple reaction monitoring (MRM)) assay for $V_HH$, each $V_HH$ was first analyzed by nanoLC-MS/MS using data-dependent acquisition to identify all ionizible peptides. For each peptide, the 3 to 5 most intense fragment ions were chosen. An initial SRM assay was developed to monitor these fragments at attomole amounts of the digest (about 100-300 amol). Fragments that showed reproducible intensity ratios at low amounts (i.e., had Pearson r2≥0.95 compared to higher amounts) were considered stable and were chosen for the final SRM assay. To further optimize the assay, elution times for each peptide were also included, with care taken to not choose peptides that have close m/z (mass-to-charge ratio) and elution times.

A typical multiplexed SRM analysis of $V_HH$ in cell media or body fluids (serum or cerebrospinal fluid (CSF)) involved spiking known amount of ILIS (0.1-10 nM) followed by injecting 100-400 ng of CSF or cultured media proteins (0.3-1 μL) or about 50-100 ng of serum proteins (1-3 nanoliters) into the nanoLC-MS system. The precursor m/z of each target peptide ion was selected in the ion trap (and the remaining unrelated ions were discarded) at the specified elution time for the target, followed by collision induced dissociation (CID) fragmentation, and selection of only the desired fragment ions in the ion trap for monitoring by the detector. For quantification analysis, raw files generated by the LTQ (ThermoFisher) were converted to the standard mass spectrometry data format mzXML and intensities were extracted using an in-house software called Q-MRM (Quantitative-MRM; see Haqqani et al. 2012), which is a modified version of MatchRx software. For each $V_HH$, extracted-ion chromatograms were generated for each of its fragment ion that consisted of combined intensities within 0.25 Da of the fragment m/z over the entire elution time. To obtain a final intensity value for each fragment, all intensities within 0.5 min of the expected retention times were summed. A $V_HH$ was defined as detectable in a sample if the fragments of at least one of its peptides showed the expected intensity ratios, i.e., the final intensity values showed a strong Pearson correlation r≥0.95 and p<0.05 compared with the final intensities values of its corresponding pure $V_HH$.

Samples containing mixtures of $V_HH$ (media, serum, CSF) were reduced, alkylated and trypsin-digested as previously described (Haqqani et al., 2012; Gergov et al., 2003). The digests (tryptic peptides) were acidified with acetic acid (5% final concentration) and analyzed on a reversed-phase nanoAcquity UPLC (Waters, Milford, Mass.) coupled to LTQ XL ETD or LTQ Orbitrap ETD mass spectrometer (ThermoFisher, Waltham, Mass.). The desired aliquot of the sample was injected and loaded onto a 300 μm I.D.×0.5 mm 3 μm PepMaps C18 trap (ThermoFisher) then eluted onto a 100 μm I.D.×10 cm 1.7 μm BEH130C18 nanoLC column (Waters) using a gradient from 0%-20% acetonitrile (in 0.1% formic) in 1 minute, 20%-46% in 16 min, and 46%-95% in 1 min at a flow rate of 400 nL/min. The eluted peptides were ionized into the mass spectrometer by electrospray ionization (ESI) for MS/MS and SRM analysis using CID for fragmentation of the peptide ions. The CID was performed with helium as collision gas at normalized collision energy of 35% and 30 ms of activation time. Ion injection times into linear ion trap were adjusted by the instrument using an automatic gain control (AGC) target value of 6×10³ and a maximum accumulation time of 200 ms.

The specific peptides used for detection and quantification of FC5-H7 CDR mutational variants are shown in Table 1.

TABLE 1

Peptides used in nanoLC-SRM detection of selected FC5-H7 CDR mutation variants In various studies described, assays were multiplexed in different combinations for simultaneous monitoring in the same sample. Limits of detection and quantification of the SRM assay for each peptide ranged from 1.5-2.5 ng/ml. 1 ng/mL corresponds to about 60-70 pM of $V_HH$. A20-1 as described in Hussack et al, 2011b).

| Protein | Signatures | SEQ ID NO: | Unique |
|---|---|---|---|
| FC5 | ITWGGDNTFYSNSVK | 20 | Yes |
| FC5-ILIS | ITWGGDNTFYSNSVK[a] | 20 | Yes |
| A20.1 | TTYYADSVK | 21 | Yes |
|  | EFVAAGSSTGR | 22 | Yes |
|  | TFSMDPMAWFR | 23 | Yes |
|  | DEYAYWGQGTQVTVSSGQAGQGSEQK | 24 | Yes |
| FC5-H7 variants | LSCAASGFK | 25 | Yes |
|  | NTLYLQMNSLR | 26 | Yes |
|  | EVQLVESGGGLVQPGGSLR | 27 | Yes |

[a] Heavy-labeled peptide.

Determination of the Apparent Permeability Coefficient:

Quantified values can be directly plotted or the $P_{app}$ (apparent permeability coefficient) values can be determined with the given formula [Qr/dt=cumulative amount in the receiver compartment versus time; A=area of the cell monolayer; C0=initial concentration of the dosing solution] and plotted. The $P_{app}$ value is commonly used to determine the ability of a molecule to cross the BBB. $P_{app}$ values are a measure of the specific permeability of the compound across brain endothelial monolayer.

Figure 6:
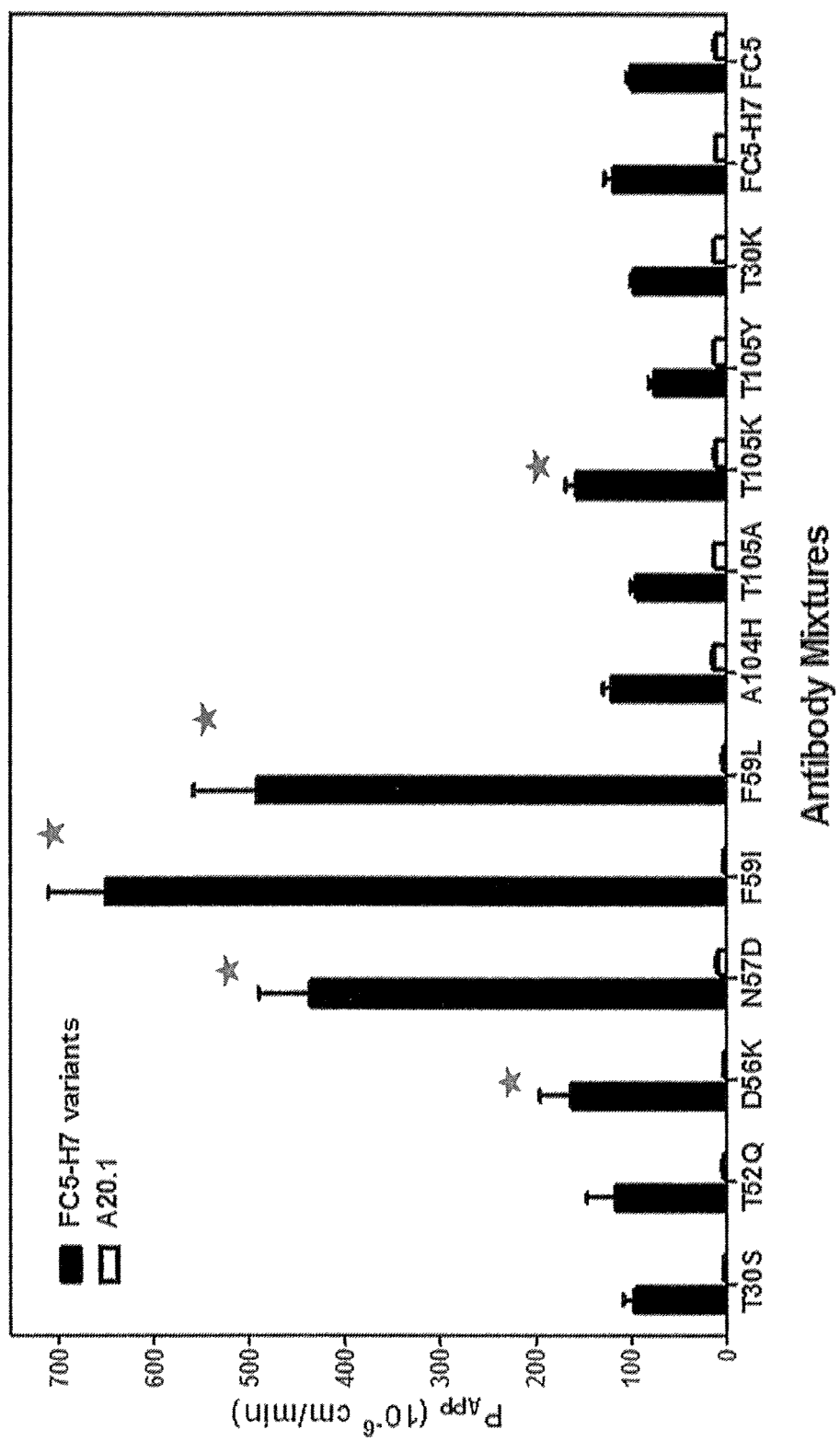
FIG. 6 shows the $P_{app}$ values obtained in in vitro BBB model of the FC5, FC5-H7 and selected FC5-H7 mutants from FIG. 5. Negative control A20.1 VHH was co-administered in top chamber together with each FC5-derived antibody and transport was measured. Asterisks indicate FC5-H7 mutants that show enhanced $P_{app}$ values compared to either FC5-H7 or FC5. Relative binding affinities of each variant were shown in the table below the graph.

The screening results for the variants with similar or higher $P_{app}$ values compared to FC5-H7 are shown in FIG. 6. These 12-15 clones were then re-expressed for detailed screening in the BBB permeability assay (full time course) as described above. Several single CDR mutation variants of FC5-H7 show significantly increased $P_{app}$ values compared to FC5-H7 indicating improvement in their rate of transport across the in vitro BBB model. Notably, mutants D56K, N57D, F59I, F59L, and T105K showed 37%, 268%, 448%, 315% and 33% higher $P_{app}$ values, respectively, compared to FC5-H7 (FIG. 6). There was no apparent correlation between binding affinities of these variants to SV-ARBEC and their transcytosis (BBB-crossing) in the in vitro BBB model using the same cells.

Example 6: Expression and Purification of FC5 Variant-Fc Constructs

Constructs comprising FC5 variants FC5, FC5-H7, D56K, N57D, F59I, F59L, and T105K $V_HH$ (FIG. 7) fused to a N-terminal of human IgG1 Fc fragment (SEQ ID NO:29) were prepared, expressed, and purified.

The FC5 variant cDNA was cloned into mammalian expression vector pTT5 (Durocher 2002) containing the human Fc fragment. Polyplexes of the resulting vector were pre-formed by mixing 25 ml of plasmid DNA solution containing 187.5 μg pTT5-IR5mFc2b, 56.25 μg pTT-AKTdd (activated mutant of Protein Kinase B), 18.75 μg pTTo-GFP (to monitor transfection efficiency), and 112.5 μg of salmon testis DNA (Sigma-Aldrich); and 25 ml of PEI solution containing 1.125 mg of PEIpro™ (PolyPlus Transfection), both made in F17 medium. The mixture was incubated for 10 minutes prior to addition to the cell culture. A 450 ml culture of CHO cells stably expressing a truncated EBNA1 protein (CHO-3E7) and grown in F17 medium (Invitrogen) was transfected with 50 ml of polyplexes. Twenty four hours post-transfection, the culture was fed with 12.5 ml of 40% (w/v) tryptone N1 (Organotechnie) solution and 1.25 ml of 200 mM valproic acid solution. The culture was harvested 8 days post-transfection and clarified by centrifugation. Clarified medium was filtered through a 0.22 µm membrane prior to its application on a column packed with 5 ml of protein-A MabSelect SuRe resin (GE Healthcare). After loading, the column was washed with 5 volumes of phosphate-buffered saline pH 7.1 (PBS) and the antibody was eluted with 100 mM sodium citrate buffer pH 3.0. Fractions containing the eluted antibody were pooled and a buffer exchange was performed by loading on a desalting Econo-Pac column (BioRad) equilibrated in PBS. Desalted antibody was then sterile-filtered by passing through a Millex GP (Millipore) filter unit (0.22 µm) and aliquoted.

Example 7: Binding of Fc-Fused FC5-H7 CDR Variants to Brain Endothelial Cells

The binding of Fc-fused FC5 CDR variants (FC5, FC5-H7, D56K, N57D, F59I, F59L, and T105K; Example 6) to rat (SV-ARBEC), human (HBEC-D3) and non-human primate (CynoBEC) brain endothelial cells was evaluated using Mirrorball® High Sensitivity Microplate Cytometry (TTP Labtech) as described in Example 4.

Figure 8:
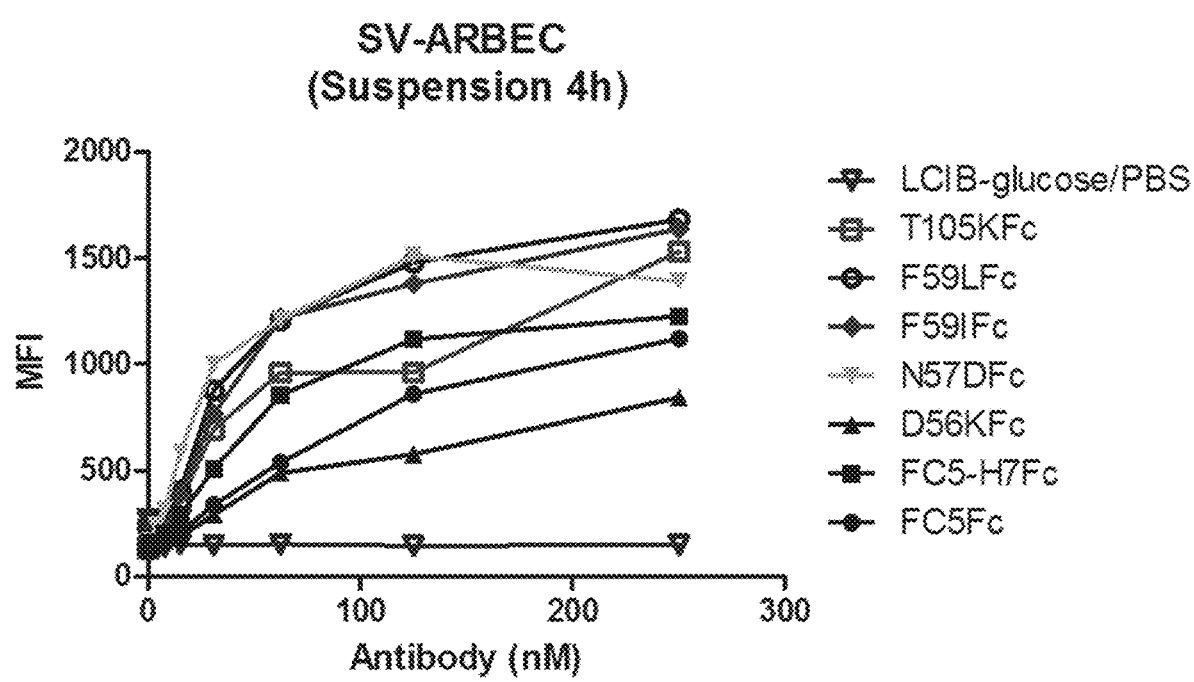
FIG. 8 shows binding of the selected FC5-H7 mutational variants (D56K, N57D, F59I, F59L, T105K), FC5-H7 and FC5, all expressed in fusion with human Fc (see sequence Table), to rat (SV-ARBEC), human (HBEC-D3) and non-human primate (CynoBEC) brain endothelial cells. Binding curves were generated with serial dilutions of each antibody using a fluorescent conjugate c-myc Alexa 488 detection antibody (1600 ng/ml, Santa Cruz Biotechnology) supplemented with Draq 5 nuclear stain (2 uM, Cell Signaling) for detection of cell-bound antibody. All plates were incubated at 4° C. for 20 h. Readings were taken at each time point using Mirrorball High Sensitivity Microplate Cytometry as described below.

The results are shown in FIG. 8. Fc fusions of variants N57D, F59I, F59L showed improved binding to brain endothelial cells from all three species (rat, human, cyno) compared to either FC5-Fc or FC5-H7-Fc. The results show species cross-reactivity of FC5 and FC5-H7 and its mutated variants.

Example 8: Transport of Fc-Fused FC5-H7 CDR Variant Across In Vitro BBB Model

To evaluate whether Fc-fused FC5-H7 CDR mutational variants (FC5, FC5-H7, D56K, N57D, F59I, F59L, and T105K) from Example 6 transmigrate the blood-brain barrier, the in vitro assay and quantification method as described in Example 5 was used.

Figure 9:
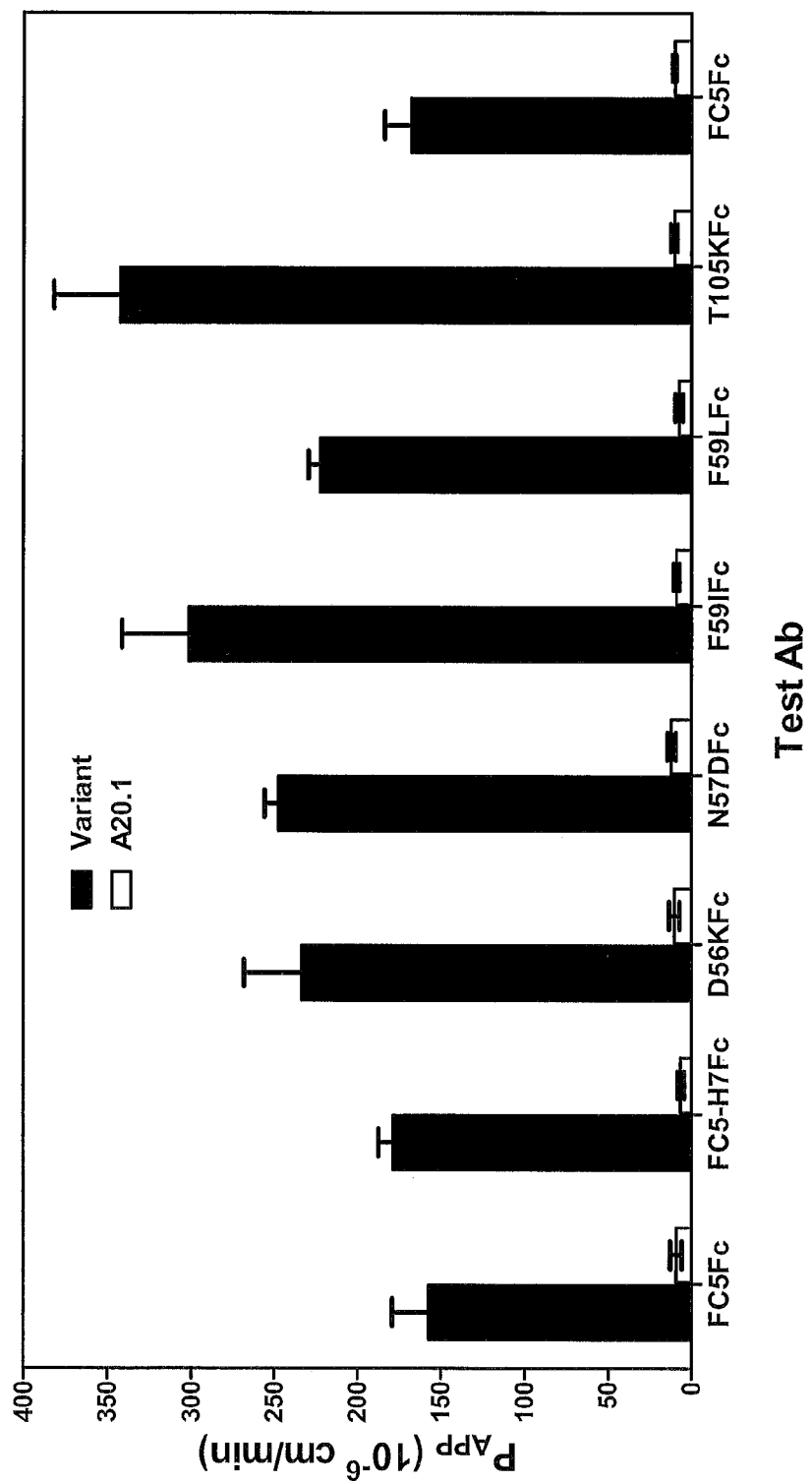
FIG. 9 shows the $P_{app}$ values in in vitro BBB model of the Fc fusions of FC5, FC5-H7 and selected affinity-optimized FC5-H7 mutational variants (D56K, N57D, F59I, F59L, T105K). Negative control A20.1 VHH was co-administered in top chamber together with each FC5-derived antibody and transport was measured. All FC5-H7 mutational variants show enhanced $P_{app}$ values compared to either FC5-H7Fc or FC5Fc.
Figure 10B:
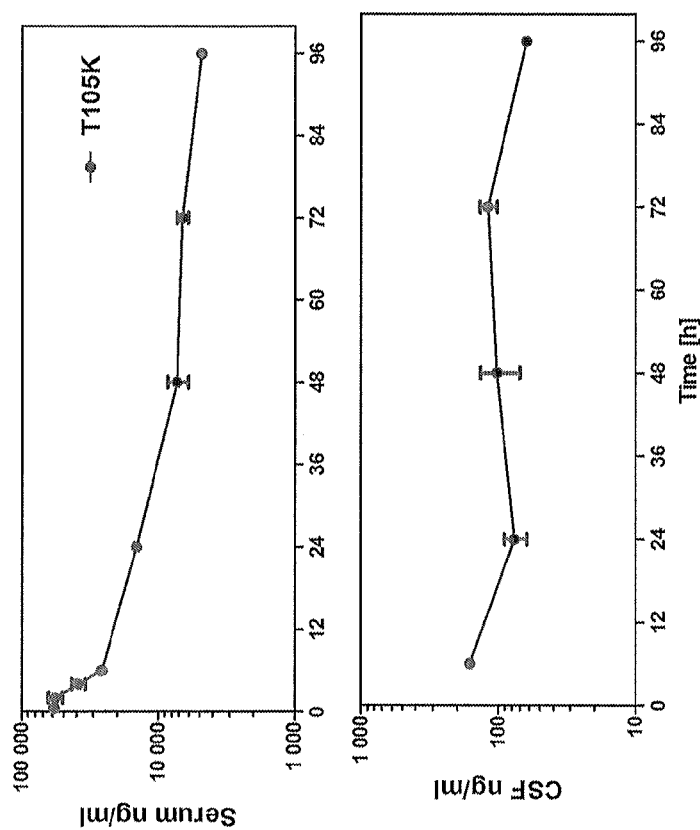
FIG. 10 shows plasma and CSF pharmacokinetics of FC5-H7-Fc (FIG. 10A), T105K-Fc (FIG. 10B), D56K-Fc (FIG. 10C), N57D-Fc (FIG. 10D), and F59L-Fc (FIG. 10E) after systemic (tail vein) administration of 5 mg/kg. The CSF was collected from cisternae magna by multiple puncture at indicated time points. Plasma and CSF concentration of antibodies were determined using the multiple reaction monitoring-isotype labeled internal standards (MRM-ILIS) method based on specific protein peptide signatures. Albumin levels in the CSF were concurrently determined by MRM. All CSF samples having a plasma/CSF ratio lower than 1500 were excluded as potentially blood-contaminated.
Figure 10A:
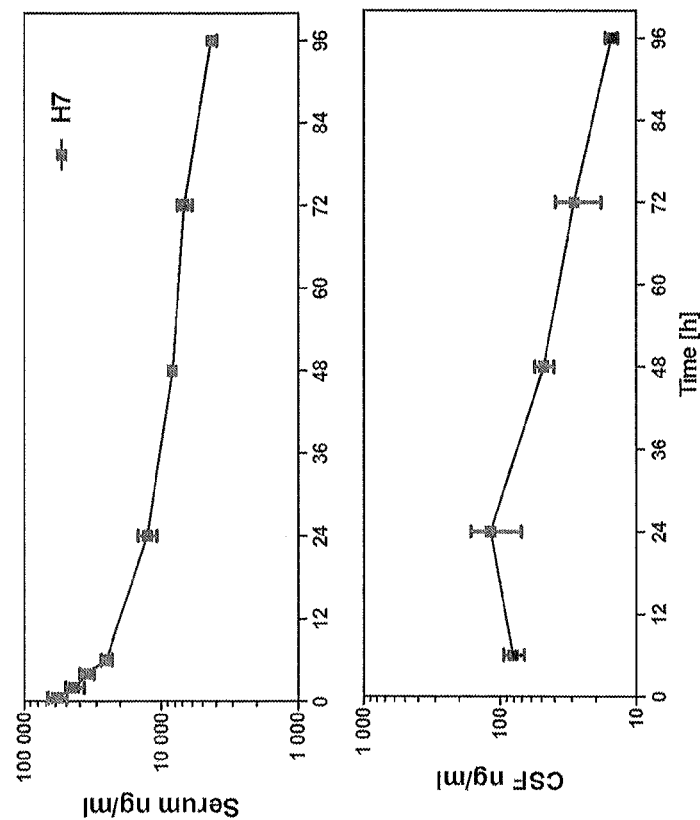
Figure 10D:
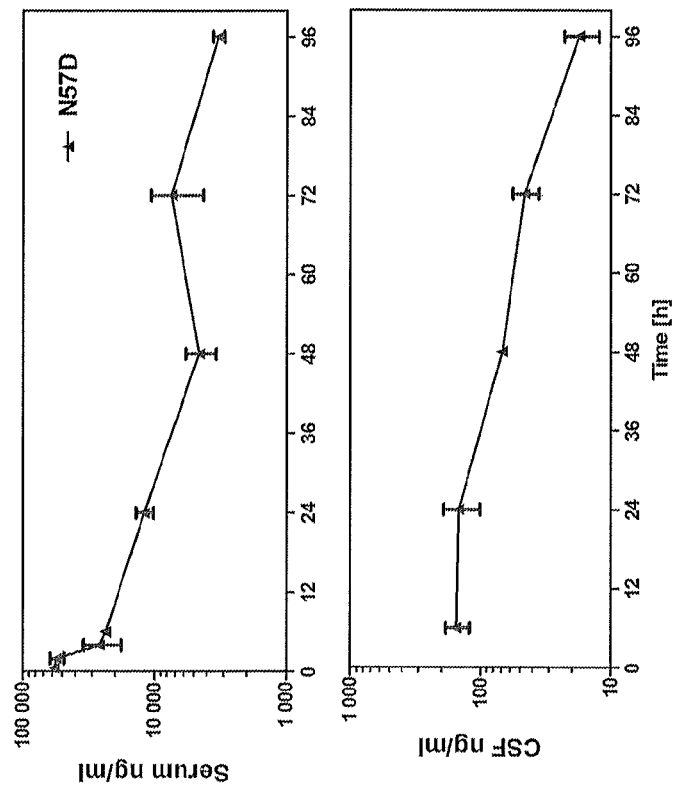
Figure 10C:
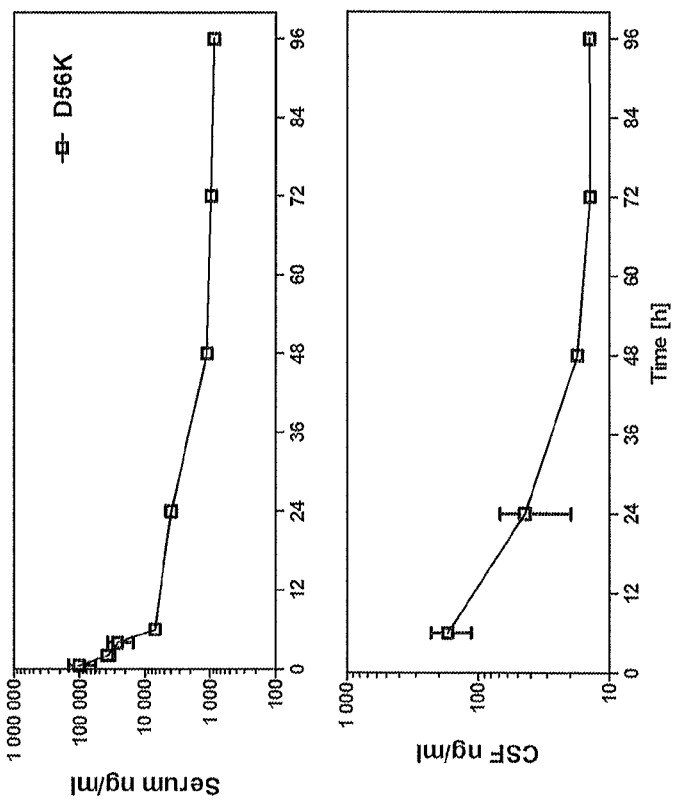
Figure 10E:
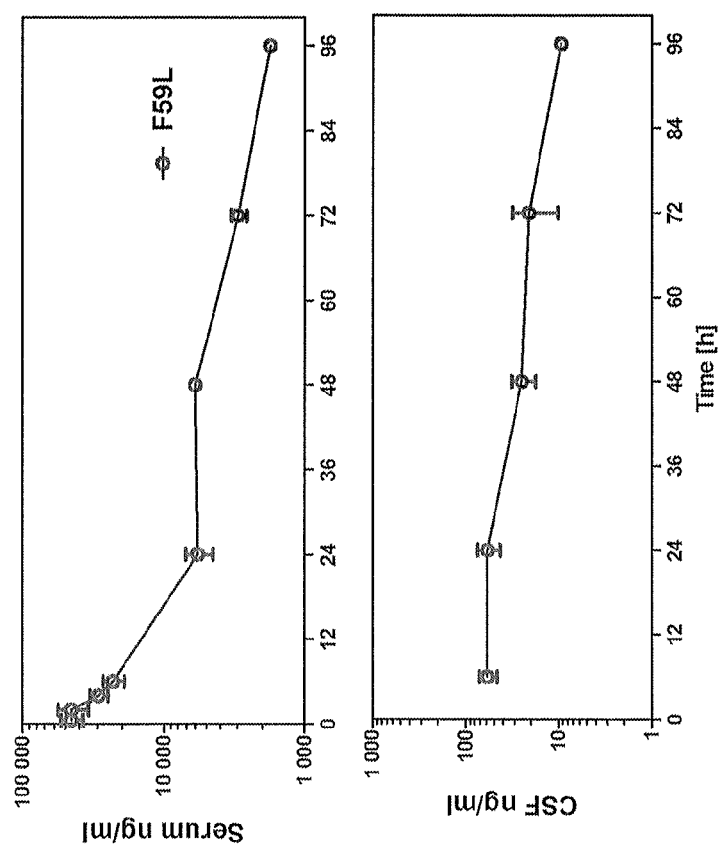

As shown in FIG. 9, D56K, N57D, F59I, F59L, and T105K variants fused to human Fc showed 31%, 39%, 69%, 25% and 92% higher $P_{app}$ compared to FC5-H7-Fc fusion. The results suggest that the improvement in affinity for selected FC5 CDR mutants resulted in enhanced BBB crossing in vitro; both affinity and BBB crossing improvements were more pronounced when variants were in monovalent $V_HH$ format then when they were expressed in bivalent Fc fusion format. Variants F59I and T105K in Fc fusion format were selected for in vivo studies.

Example 9: Pharmacokinetics of FC5 CDR Variants-Fc Fusions in CSF and Plasma

An in vivo assay was carried out to determine whether Fc fusions with FC5-H7 mutated variants F59I and T105K are able to cross into the brain, and specifically into the cerebrospinal fluid (CSF), as well as to quantify its presence in CSF and serum.

The technique used for multiple sampling of cisterna magna CSF was developed at NRC by modification of previously described methods (Huang et al., 1995; Kornhuber et al., 1986). All animals were purchased from Charles River Laboratories International, Inc. (Wilmington, Mass., USA). Animals were housed in groups of three in a 12 h light/dark cycle at a temperature of 24° C., a relative humidity of 50±5%, and were allowed free access to food and water. All animal procedures were approved by the NRC's Animal Care Committee and were in compliance with the Canadian Council of Animal Care guidelines. Male Wistar rats aged 8-10 weeks (weight range, 230-250 g) were used in all studies.

In all experiments, test antibodies (FC5-H7 mutant Fc-fusions) were administered i.v. into tail vein in equimolar doses (7 mg/kg). CSF sample collections were made from cisterna magna by needle puncture up to five times over 96 hours. For sample collection rats were briefly and lightly anesthetized with 3% isoflurane, placed in a stereotaxic frame with the head rotated downward at a 45° angle. A 2-cm midline incision between the ears beginning at the occipital crest was made and muscles separated to expose dura mater covering cisternae magna. A 27G butterfly needle (QuickMedical, Cat # SV27EL) with tubing attached to 1 ml syringe was used to puncture dura and aspirate the ~20 µl of CSF. The CSF was then transferred into the sample glass vial (Waters, Cat #186000384c) and placed in −80° C. freezer until further analysis.

Blood samples were collected from the tail vein in a commercially available tube (BD microtainer, Cat #365956). After clotting at room temperature for 15-30 minutes, the clot was removed by centrifuging at 1100 rcf (3422 rpm) for 10 min; serum was then transferred into a clean glass vial (Waters, Cat #186000384c), frozen on dry ice and stored at −80° C. until further analysis. At the end of collection, rats were sacrificed by cardiac puncture. Blood and CSF PK analyses were performed using WinLin 6.0 program.

Serum and CSF samples were analyzed by mass spectrometry and nanoLC-SRM based quantification as described in Example 5 using peptide signatures shown in Table 1.

CSF collection is a delicate procedure during which CSF can be easily contaminated with blood. Since the amounts of $V_HH$ s were expected to be much smaller in the CSF (<0.1%) than blood, even a slight contamination with blood could seriously compromise the value of an individual CSF sample. It was therefore necessary to develop stringent exclusion criteria for blood-contaminated CSF samples. To evaluate blood-CSF albumin ratio, a nanoLC-SRM method was developed for quantifying albumin levels in plasma and CSF. An albumin peptide APQVSTPTLVEAAR (SEQ ID NO:28) was selected based on its unique retention time and m/z value (Mol Pharm) in order to have minimum interference with other peptide peaks in the multiplex assay. The intensity of the peptide was quantified in both CSF and plasma samples using SRM as described above. The albumin ratio was calculated as follows for each rat:

Albumin Ratio=Intensity per nL of plasma analyzed/ Intensity per nL of CSF analyzed A ratio of 1500 and below was considered as blood contaminated.

Results are shown in FIG. 10 and Table 2. CSF/serum area under the curve (AUC) ratio for each molecule was indicative of CSF 'exposure' of the variant over a 96 h period. Each Fc-fusion molecule carrying FC5 mutational variant showed higher (15-35-fold) CSF exposure compared to control $V_HH$-Fc fusion molecule (A20.1Fc). Furthermore, T105K-Fc, D56K-Fc and N57D-Fc showed increased CSF exposure (~2-fold), whereas F59L-Fc shows similar CSF exposure compared to parent FC5H7-Fc. These results established that CDR mutational variants of FC5-H7 have the same or improved CSF exposure profile in vivo. In particular, T105K-Fc, D56K-Fc, and N57D-Fc also demonstrated improved BBB-crossing properties in in vitro rat BBB model (FIG. 9), consistent with the observed enhanced CSF exposure in vivo.

TABLE 2

Serum and CSF exposure (area under Curve-AUC) of systemically injected
FC5-H7 CDR mutant variant-Fc fusions and A20.1Fc (from FIG. 9).

| Variant | H7 | T105K | D56K | N57D | F59L | A20.1 |
|---|---|---|---|---|---|---|
| Serum | 1127000 | 1180000 | 410855 | 975072 | 761068 | 1740399 |
| CSF | 5246 | 9122 | 3395 | 7438 | 2969 | 941 |
| CSF/Serum AUC ratio | 0.465 | 0.773 | 0.826 | 0.762 | 0.390 | 0.022 |

Example 10. Brain Levels of Fc-Fused FC5-H7 CDR Mutants after Systemic Administration In separate experiments, FC5-H7-Fc, F59I-Fc, T105K-Fc, D56K-Fc, N57D-Fc, F59L-Fc and A20.1-Fc were administered by i.v. injection via tail vein, each at 7 mg/kg, and circulated for 24 h. Rats were then thoroughly perfused with 10 ml of heparinized (100 U/ml) saline at a rate of 1 ml/min via the left common carotid artery to facilitate specific perfusion of the brain. Brains were then removed and homogenized in ice-cold homogenization buffer containing 50 mM Tris-HCl pH 8, 150 mM NaCl and protease inhibitor cocktail (Sigma-Aldrich, Oakville, ON) using Dounce homogenizer (10-12 stroke at 4° C.). Samples were then sonicated three times for 10 s each at 4° C. and insoluble material was removed (10,000×g for 10 min at 4° C.). The supernatant was analyzed for protein content, and about 0.5 µg of protein was used for SRM analysis using methods described in Example 5 and peptide signatures shown in Table 1.

Figure 11:
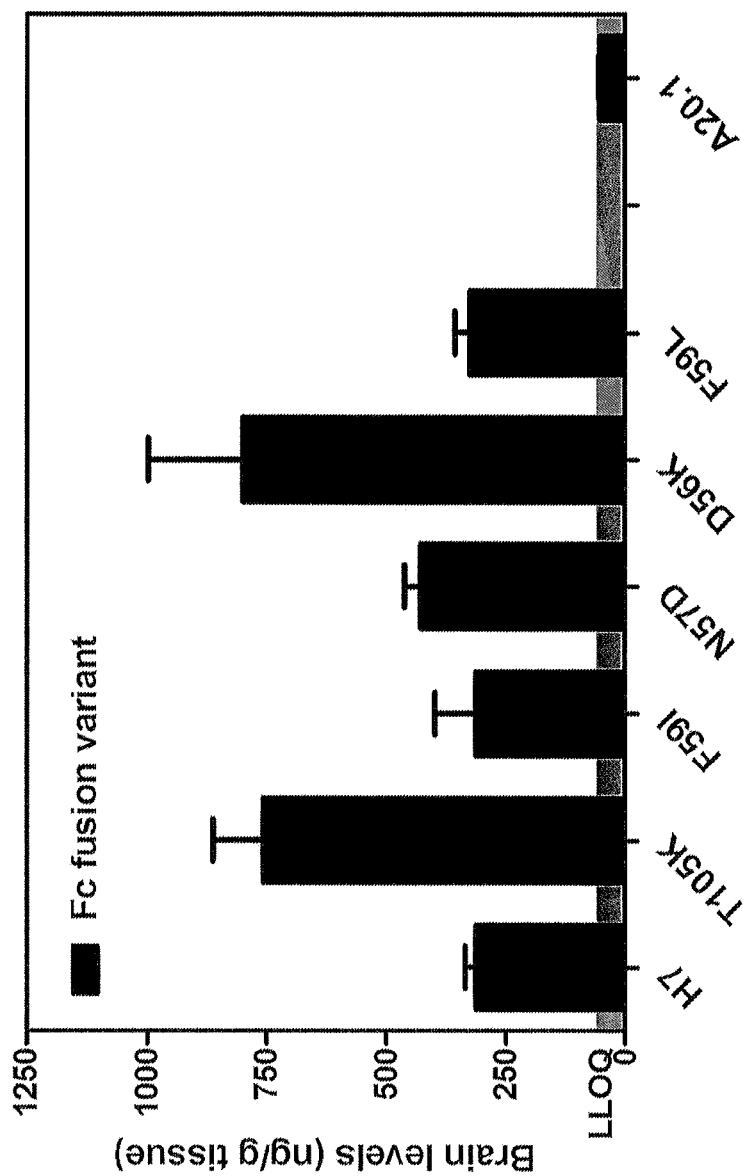
FIG. 11 shows brain levels of FC5-H7-Fc, D56K-Fc, N57D-Fc, F59L-Fc, T105K-Fc and control A20.1 mouse Fc fusion (A20.1-mFc) after systemic (tail vein) administration of 5 mg/kg. Brain levels were determined after brain perfusion through carotid artery using the MRM-ILIS method that quantifies specific protein peptide signatures. The results are mean±SD for 3 animals per group and 2 separate analytical determinations.

The results are shown in FIG. 11. All Fc-fused FC5 mutational variants (FC5-H7-Fc, F59I-Fc, T105K-Fc, D56K-Fc, N57D-Fc, F59L-Fc) had significantly higher (6-15-fold) brain levels 24 h after administration compared to control article, A20.1Fc. Compared to the parent FC5-H7-Fc variant, CDR mutational variants T105K-Fc, D56K-Fc and N57D-Fc, showed approximately 2-fold higher brain levels 24 h after administration of the same dose. F59I-Fc and F59L-Fc had brain levels similar to FC5-H7-Fc. The results demonstrated that some mutational variants of FC5-H7 exhibited better brain penetration and achieved higher brain levels compared to parent variant. The results also demonstrated that improved binding affinity to brain endothelial cells was not sufficient to predict improved BBB crossing and higher brain exposure of selected variants either in vitro or in vivo. For example, variants N57D, F59I and F59L had similar binding properties to rat brain endothelial cells and higher affinity binding than T105K and D56K, yet N57D and T105K showed the best BBB crossing and brain exposure in vivo.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

SEQUENCES

| SEQ ID NO: | Sequence | Description |
|---|---|---|
| 1 | GFKITHYTMG | CDR1 FC5 |
| 2 | RITWGGX$_1$X$_2$TX$_3$YSNSVKG | CDR2 consensus |
| 3 | GSTSTAX$_4$PLRVDY | CDR3 consensus |
| 4 | RITWGGDNTFYSNSVKG | CDR2 FC5 |
| 5 | RITWGGKNTFYSNSVKG | CDR2 D56K |
| 6 | RITWGGDDTFYSNSVKG | CDR2 N57D |
| 7 | RITWGGDNTIYSNSVKG | CDR2 F59I |
| 8 | RITWGGDNTLYSNSVKG | CDR2 F59L |
| 9 | GSTSTAKPLRVDY | CDR3 T105K |
| 10 | GSTSTATPLRVDY | CDR3 FC5 |
| 11 | EVQLVESGGGLVQPGGSLRLSCAASGFKITHYTMGWFRQAPG KEREFVSRITWGGDNTFYSNSVKGRFTISRDNSKNTLYLQMNS LRAEDTAVYYCAAGSTSTAKPLRVDYWGQGTLVTVSS | FC5-H7-T105K |
| 12 | EVQLVESGGGLVQPGGSLRLSCAASGFKITHYTMGWFRQAPG KEREFVSRITWGGKNTFYSNSVKGRFTISRDNSKNTLYLQMNSL RAEDTAVYYCAAGSTSTATPLRVDYWGQGTLVTVSS | FC5-H7-D56K |

| SEQ ID NO: | Sequence | Description |
|---|---|---|
| 13 | EVQLVESGGGLVQPGGSLRLSCAASGFKITHYTMGWFRQAPG KEREFVSRITWGGDDTFYSNSVKGRFTISRDNSKNTLYLQMNS LRAEDTAVYYCAAGSTSTATPLRVDYWGQGTLVTVSS | FC5-H7-N57D |
| 14 | EVQLVESGGGLVQPGGSLRLSCAASGFKITHYTMGWFRQAPG KEREFVSRITWGGDNTIYSNSVKGRFTISRDNSKNTLYLQMNSL RAEDTAVYYCAAGSTSTATPLRVDYWGQGTLVTVSS | FC5-H7-F59I |
| 15 | EVQLVESGGGLVQPGGSLRLSCAASGFKITHYTMGWFRQAPG KEREFVSRITWGGDNTLYSNSVKGRFTISRDNSKNTLYLQMNSL RAEDTAVYYCAAGSTSTATPLRVDYWGQGTLVTVSS | FC5-H7-F59L |
| 16 | DVQLQASGGGLVQAGGSLRLSCAASGFKITHYTMGWFRQAPG KEREFVSRITWGGDNTFYSNSVKGRFTISRDNAKNTVYLQMNS LKPEDTADYYCAAGSTSTATPLRVDYWGKGTQVTVSS | FC5 |
| 17 | EVQLVESGGGLVQPGGSLRLSCAASGFKITHYTMGWFRQAPG KEREFVSRITWGGDNTFYSNSVKGRFTISRDNSKNTLYLQMNS LRAEDTAVYYCAAGSTSTATPLRVDYWGQGTLVTVSS | FC5-H7 |
| 18 | GTGAAAAAATTATTATTATTCGCAATTCCT | fdTGIII primer |
| 19 | CCCTCATAGTTAGCGTAACG | 96G III primer |
| 20 | ITWGGDNTFYSNSVK | FC5 peptide |
| 21 | TTYYADSVK | A20.1 peptide |
| 22 | EFVAAGSSTGR | A20.1 peptide |
| 23 | TFSMDPMAWFR | A20.1 peptide |
| 24 | DEYAYWGQGTQVTVSSGQAGQGSEQK | A20.1 peptide |
| 25 | LSCAASGFK | FC5-H7 variant peptide |
| 26 | NTLYLQMNSLR | FC5-H7 variant peptide |
| 27 | EVQLVESGGGLVQPGGSLR | FC5-H7 variant peptide |
| 28 | APQVSTPTLVEAAR | Albumin peptide |
| 29 | AEPKSCDKTHTCPPCPAPELLGGPSVFLFPPKPKDTLMISRTPE VTCVVVDVSHEGPEVKFNWVDGVEVHNAKTKPREEQYNSTY RVVSVLTVLHQDWLNGKEYKCKVSNKALPAPIEKTISKAKGQPR EPQVYTLPPSRDELTKNQVSLTCLVKGFYPSDIAVEWESNGQP ENNYKTTPPVLDSDGSFFLYSKLTVDKSRWQQGNVFSCSVMH EGLHNHYTQKSLSLSPG | IgG1 Fc |
| 30 | GAGGTCCAGCTGGTGGAATCTGGAGGAGGATTGGTGCAGCC GGGGGGCTCTCTGAGACTCTCCTGTGCAGCCTCTGGATTCA AAATCACTCACTATACCATGGGCTGGTTCCGCCAGGCTCCAG GGAAGGAGCGTGAATTTGTATCACGTATTACTTGGGGTGGTG ATAACACCTTCTATTCAAACTCCGTGAAGGGCCGATTCACCA TTTCCAGAGACAACAGCAAGAACACGCTGTATCTGCAAATGA ACAGCCTGCGTGCGGAGGACACGGCCGTGTATTACTGTGCA GCAGGTTCGACGTCGACTGCGAAACCACTTAGGGTGGACTA CTGGGGCCAGGGGACCCTGGTCACCGTCTCCTCA | FC5-H7-T105K |
| 31 | GAGGTCCAGCTGGTGGAATCTGGAGGAGGATTGGTGCAGCC GGGGGGCTCTCTGAGACTCTCCTGTGCAGCCTCTGGATTCA AAATCACTCACTATACCATGGGCTGGTTCCGCCAGGCTCCAG GGAAGGAGCGTGAATTTGTATCACGTATTACTTGGGGTGGTA AAAACACCTTCTATTCAAACTCCGTGAAGGGCCGATTCACCA TTTCCAGAGACAACAGCAAGAACACGCTGTATCTGCAAATGA ACAGCCTGCGTGCGGAGGACACGGCCGTGTATTACTGTGCA GCAGGTTCGACGTCGACTGCGACGCCACTTAGGGTGGACTA CTGGGGCCAGGGGACCCTGGTCACCGTCTCCTCA | FC5-H7-D56K |

SEQUENCES

| SEQ ID NO: | Sequence | Description |
|---|---|---|
| 32 | GAGGTCCAGCTGGTGGAATCTGGAGGAGGATTGGTGCAGCC<br>GGGGGGCTCTCTGAGACTCTCCTGTGCAGCCTCTGGATTCA<br>AAATCACTCACTATACCATGGGCTGGTTCCGCCAGGCTCCAG<br>GGAAGGAGCGTGAATTTGTATCACGTATTACTTGGGGTGGTG<br>ATGATACCTTCTATTCAAACTCCGTGAAGGGCCGATTCACCA<br>TTTCCAGAGACAACAGCAAGAACACGCTGTATCTGCAAATGA<br>ACAGCCTGCGTGCGGAGGACACGGCCGTGTATTACTGTGCA<br>GCAGGTTCGACGTCGACTGCGACGCCACTTAGGGTGGACTA<br>CTGGGGCCAGGGGACCCTGGTCACCGTCTCCTCA | FCS-H7-N57D |
| 33 | GAGGTCCAGCTGGTGGAATCTGGAGGAGGATTGGTGCAGCC<br>GGGGGGCTCTCTGAGACTCTCCTGTGCAGCCTCTGGATTCA<br>AAATCACTCACTATACCATGGGCTGGTTCCGCCAGGCTCCAG<br>GGAAGGAGCGTGAATTTGTATCACGTATTACTTGGGGTGGTG<br>ATAACACCATCTATTCAAACTCCGTGAAGGGCCGATTCACCA<br>TTTCCAGAGACAACAGCAAGAACACGCTGTATCTGCAAATGA<br>ACAGCCTGCGTGCGGAGGACACGGCCGTGTATTACTGTGCA<br>GCAGGTTCGACGTCGACTGCGACGCCACTTAGGGTGGACTA<br>CTGGGGCCAGGGGACCCTGGTCACCGTCTCCTCA | FCS-H7-F59I |
| 34 | GAGGTCCAGCTGGTGGAATCTGGAGGAGGATTGGTGCAGCC<br>GGGGGGCTCTCTGAGACTCTCCTGTGCAGCCTCTGGATTCA<br>AAATCACTCACTATACCATGGGCTGGTTCCGCCAGGCTCCAG<br>GGAAGGAGCGTGAATTTGTATCACGTATTACTTGGGGTGGTG<br>ATAACACCCTGTATTCAAACTCCGTGAAGGGCCGATTCACCA<br>TTTCCAGAGACAACAGCAAGAACACGCTGTATCTGCAAATGA<br>ACAGCCTGCGTGCGGAGGACACGGCCGTGTATTACTGTGCA<br>GCAGGTTCGACGTCGACTGCGACGCCACTTAGGGTGGACTA<br>CTGGGGCCAGGGGACCCTGGTCACCGTCTCCTCA | FCS-H7-F59L |
| 35 | GAGGTCCAGCTGGTGGAATCTGGAGGAGGATTGGTGCAGCC<br>GGGGGGCTCTCTGAGACTCTCCTGTGCAGCCTCTGGATTCA<br>AAATCACTCACTATACCATGGGCTGGTTCCGCCAGGCTCCAG<br>GGAAGGAGCGTGAATTTGTATCACGTATTACTTGGGGTGGTG<br>ATAACACCTTCTATTCAAACTCCGTGAAGGGCCGATTCACCA<br>TTTCCAGAGACAACAGCAAGAACACGCTGTATCTGCAAATGA<br>ACAGCCTGCGTGCGGAGGACACGGCCGTGTATTACTGTGCA<br>GCAGGTTCGACGTCGACTGCGACGCCACTTAGGGTGGACTA<br>CTGGGGCCAGGGGACCCTGGTCACCGTCTCCTCA | FC5-H7 |

REFERENCES

All patents, patent applications and publications referred to herein and throughout the application are hereby incorporated by reference.

Abbott N J (2013) Blood-brain barrier structure and function and the challenges for CNS drug delivery. J Inherit Metab Dis. 36(3):437-49.

Abulrob A, Sprong H, Van Bergen en Henegouwen P, Stanimirovic D (2005) The blood-brain barrier transmigrating single domain antibody: mechanisms of transport and antigenic epitopes in human brain endothelial cells. J Neurochem. 95(4):1201-14.

Arbabi-Ghahroudi, M. Desmyter A, Wyns L, Hamers R., and Muyldermans S (1997) Selection and identification of single domain antibody fragments from camel heavy-chain antibodies, FEBS Lett 414, 521-526

Bell A., Wang Z. J., Arbabi-Ghahroudi M., Chang T. A., Durocher Y., Trojahn U., Baardsnes J., Jaramillo M. L., Li S., Baral T. N., O'Connor-McCourt M., Mackenzie R., and Zhang J. (2010) Cancer Lett. 289, 81-90.

Chothia C., and Lesk A. M. (1987) J. Mol. Biol. 196, 901-917.

Davies J., and L. Riechmann, Affinity improvement of single antibody VH domains: residues in all three hypervariable regions affect antigen binding. Immunotechnology 2 (1996) 169-179

De Kruif, J., and Logtenberg, T. (1996) J. Biol. Chem. 271, 7630-7634.

Demeule M.; Currie J. C.; Bertrand Y.; Che C.; Nguyen T.; Regina A.; Gabathuler R.; Castaigne J. P.; Beliveau R. Involvement of the low-density lipoprotein receptor-related protein in the transcytosis of the brain delivery vector angiopep-2, J. Neurochem. 2008, 106, 1534-1544.

Dumoulin, M., Conrath, K., Van Meirhaighe, A., Meersman, F., Heremans, K., Frenken, L. G., Muyldermans, S., Wyns, L., and Matagne, A. (2002) Protein Sci 11, 500-515.

Eisenberg, D., Schwarz, E., Komaromy, M., and Wall, R. (1984) J. Mol. Biol. 179, 125-142

Erdlenbruch B, Alipour M, Fricker G, Miller D S, Kugler W, Eibl H, Lakomek M (2003) Alkylglycerol opening of the blood-brain barrier to small and large fluorescence markers in normal and C6 glioma-bearing rats and isolated rat brain capillaries. Br J Pharmacol. 140(7):1201-10.

Gan Y, Jing Z, Stetler R A, Cao G (2013) Gene delivery with viral vectors for cerebrovascular diseases. Front Biosci (Elite Ed). 5:188-203. Review.

Garberg, P.; Ball, M.; Borg, N.; Cecchelli, R.; Fenart, L.; Hurst, R. D.; Lindmark, T.; Mabondzo, A.; Nilsson, J. E.; Raub, T. J.; Stanimirovic, D.; Terasaki, T.; Oberg, J. O.; Osterberg, T. In vitro models for the blood-brain barrier, Toxicol. In Vitro 2005, 19, 299-334.

Gergov, M.; Ojanpera, I.; Vuori, E. Simultaneous screening for 238 drugs in blood by liquid chromatography-ion spray tandem mass spectrometry with multiple-reaction monitoring, J. Chromatogr. B Analyt. Technol. Biomed. Life Sci. 2003, 795, 41-53.

Gonzales N R, DePascalis R, Schlom J, Kashmiri S V S (2005) Tumor Biol 26, 31-43.

Gottesman et al., Ann. Rev. Biochem., 62, 385-427 (1993)

Guillaume D J et al. Intra-arterial chemotherapy with osmotic blood-brain barrier disruption for aggressive oligodendroglial tumors: results of a phase I study. Neurosurgery, 66(1), 48-58 (2010).

Hamers-Casterman, C., Atarhouch, T., Muyldermans, S., Robinson, G., Hamers, C., Songa, E. B., Bendahman, N., and Hamers, R. (1993) Nature 363, 446-448.

Haqqani A S, Caram-Salas N, Ding W, Brunette E, Delaney C E, Baumann E, Boileau E, Stanimirovic D (2012) Multiplexed evaluation of serum and CSF pharmacokinetics of brain-targeting single-domain antibodies using a NanoLC-SRM-ILIS method. Mol Pharm. 2013 May 6; 10(5):1542-56.

Huang Y L, Säljö, Suneson A, Hansson H A (1995) A new approach for multiple sampling of cisternal cerebrospinal fluid in rodents with minimal trauma and inflammation. J Neurosci Methods. 63(1-2):13-22.

Hussack G., Hirama T., Ding W., MacKenzie R., and Tanha J. (2011) PLoS ONE 6, e28218.

Hussack G, Arbabi-Ghahroudi M, van Faassen H, Songer J G, Ng K K, MacKenzie R, Tanha J (2011b) Neutralization of Clostridium difficile toxin A with single-domain antibodies targeting the cell receptor binding domain. J Biol Chem. 286(11): 8961-76.

Iqbal U., Trojahn U., Albaghdadi H., Zhang J., O'Connor M., Stanimirovic D., Tomanek B., Sutherland G., and Abulrob A. (2010) Br. J. Pharmacol. 160, 1016-1028.

Jespers, L., Schon, O., Famm, K., and Winter, G. (2004) Nat. Biotechnol. 22, 1161-1165.

Jones P T, Dear P H, Foote J, Neuberger M S, Winter G (1986) Nature 321, 522-525.

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19.

Kim, D. Y., Kandalaft, H., Ding, W., Ryan, S., van Fassen, H., Hirama, T., Foote, S. J., MacKenzie, R., and Tanha, J. (2012) PEDS advance access Aug. 30, 2012, 1-9.

Kornhuber M E, Kornhuber J, Cimniak U (1986) A method for repeated CSF sampling in the freely moving rat. J Neurosci Methods. 17(1):63-8.

Li S, Zheng W, Kuolee R, Hirama T, Henry M, Makvandi-Nejad S, Fjallman T, Chen W, Zhang J. Pentabody-mediated antigen delivery induces antigen-specific mucosal immune response. Mol Immunol 2009; 46:1718-26.

Merritt, E. A., and Hol, W. G. (1995) Curr. Opin. Struct. Biol. 5, 165-171.

Muruganandam A, Tanha J, Narang S, Stanimirovic D (2001) Selection of phage-displayed llama single-domain antibodies that transmigrate across human blood-brain barrier endothelium. FASEB J. February; 16(2):240-2.

Nhan T, Burgess A, Cho E E, Stefanovic B, Lilge L, Hynynen K. (2013) Drug delivery to the brain by focused ultrasound induced blood-brain barrier disruption: Quantitative evaluation of enhanced permeability of cerebral vasculature using two-photon microscopy. J Control Release. 172(1):274-280.

Nicaise M, Valeio-Lepiniec M, Minard P, Desmadril M. (2004) Affinity transfer by CDR grafting on a nonimmunoglobulin scaffold. Protein Sci. 13(7): 1882-1891.

Nielsen, U. B., Adams, G. P., Weiner, L. M., and Marks, J. D. (2000) Cancer Res. 60, 6434-6440.

Nuttall, S. D., Krishnan, U. V., Doughty, L., Pearson, K., Ryan, M. T., Hoogenraad, N. J., Hattarki, M., Carmichael, J. A., Irving, R. A., and Hudson, P. J. (2003) Eur. J. Biochem. 270, 3543-3554.

Padlan E A (1991) A possible procedure for reducing the immunogenicity of antibody variable domains while preserving their ligand-binding properties. Mol Immunol 28, 489-498.

Pardridge, W. M.; Buciak, J. L.; Friden, P. M. Selective transport of an anti-transferrin receptor antibody through the blood-brain barrier in vivo, J. Pharmacol. Exp. Ther. 1991, 259, 66-70.

Pardridge, W. M., Adv. Drug Delivery Reviews, 15, 5-36 (1995)

Pardridge, W. M. Drug and gene delivery to the brain: the vascular route, Neuron. 2002, 36, 555-558.

Preston E, Slinn J, Vinokourov I, Stanimirovic D. (2008) Graded reversible opening of the rat blood-brain barrier by intracarotid infusion of sodium caprate. J Neurosci Methods. 168(2):443-9.

Queen C, Schneider W P, Selick H E, Payne P W, Landolfi N F, Duncan J F, Avdalovic N M, Levitt M, Junghans R P, Waldmann T A (1989) Proc Natl Acad Sci USA 86, 10029-10033.

Ridgway, J. B., Presta, L. G., and Carter, P. (1996) Protein Eng. 9, 617-621.

Riechmann L, Clark M, Waldmann H, Winter G (1988) Nature 332, 323-327.

Samuels B. L., J. Clin. Pharmacol. Ther., 54, 421-429 (1993)

Sumbria R K, Zhou Q H, Hui E K, Lu J Z, Boado R J, Pardridge W M. (2013) Pharmacokinetics and brain uptake of an IgG-TNF decoy receptor fusion protein following intravenous, intraperitoneal, and subcutaneous administration in mice. Mol Pharm. 10(4):1425-31.

Tempest P R, Bremmer P, Lambert M, Taylor G, Furze J M, Carr F J, Harris W J (1991) Biotechnology 9, 266-271.

To, R., Hirama, T., Arbabi-Ghahroudi, M., MacKenzie, R., Wang, P., Xu, P., Ni, F., and Tanha, J. (2005) J. Biol. Chem. 280, 41395-41403.

Tsurushita N, Hinton, R P, Kumar S (2005) Design of humanized antibodies: From anti-Tac to Zenapax. Methods 36, 69-83.

Watanabe, T., Acta Oncol., 34, 235-241 (1995)

Xiao G, Gan L S. (2013) Receptor-mediated endocytosis and brain delivery of therapeutic biologics. Int J Cell Biol. doi: 10.1155/2013/703545. Epub 2013 Jun. 11. Yaksh T L, Rudy T A (1976) Chronic catheterization of the spinal subarachnoid space. Physiol Behav. 17(6):1031-6.

Yu, Y. J.; Zhang, Y.; Kenrick, M.; Hoyte, K.; Luk, W.; Lu, Y.; Atwal, J.; Elliott, J. M.; Prabhu, S.; Watts, R. J.; Dennis, M. S. Boosting brain uptake of a therapeutic antibody by reducing its affinity for a transcytosis target, Sci. Transl. Med. 2011, 3, 84ra44.

Zhu et al., Immunology and Cell Biology (2010) 88:667-675.

WO 95/04069
WO/2004/076670
WO2003/046560
WO 2002/057445
WO 2011/127580
WO 2007/036021

The invention claimed is:

1. An isolated or purified antibody fragment, comprising:
   a complementarity determining region (CDR) 1 sequence of GFKITHYTMG (SEQ ID NO:1);
   a CDR2 sequence of RITWGGX$_1$X$_2$TX$_3$YSNSVKG (SEQ ID NO:2), where X$_1$ is D or K, X$_2$ is N or D, and X3 is F, I or L; and
   a CDR3 sequence of GSTSTAX$_4$PLRVDY (SEQ ID NO:3), where X$_4$ is T or K, wherein at least one of the amino acid residues at positions X$_1$, X$_2$, X$_3$ or X$_4$ is different from the corresponding residue in CDR2 (SEQ ID NO:4) or CDR3 (SEQ ID NO:10) of SEQ ID NO:16.

2. The isolated or purified antibody fragment of claim 1, wherein CDR2 is selected from the group consisting of RITWGGDNTFYSNSVKG (SEQ ID NO:4), RITWGGKNTFYSNSVKG (SEQ ID NO:5), RITWGGDDTFYSNSVKG (SEQ ID NO:6), RITWGGDNTIYSNSVKG (SEQ ID NO:7), and RITWGGDNTLYSNSVKG (SEQ ID NO:8); with the proviso that if the CDR2 sequence is RITWGGDNTFYSNSVKG (SEQ ID NO:4), CDR3 is not GSTSTATPLRVDY (SEQ ID NO:10).

3. The isolated or purified antibody fragment of claim 1, wherein CDR3 is GSTSTAKPLRVDY (SEQ ID NO:9) or GSTSTATPLRVDY (SEQ ID NO:10); with the proviso that if CDR3 sequence is GSTSTATPLRVDY (SEQ ID NO:10), CDR2 is not RITWGGDNTFYSNSVKG (SEQ ID NO:4).

4. The isolated or purified antibody fragment of claim 1, comprising:
   a CDR1 sequence of GFKITHYTMG (SEQ ID NO:1), a CDR2 sequence of RITWGGDNTFYSNSVKG (SEQ ID NO:4), and a CDR3 sequence of GSTSTAKPLRVDY (SEQ ID NO:9);
   a CDR1 sequence of GFKITHYTMG (SEQ ID NO:1), a CDR2 sequence of RITWGGKNTFYSNSVKG (SEQ ID NO:5), and a CDR3 sequence of GSTSTATPLRVDY (SEQ ID NO:10);
   a CDR1 sequence of GFKITHYTMG (SEQ ID NO:1), a CDR2 sequence of RITWGGDDTFYSNSVKG (SEQ ID NO:6), and a CDR3 sequence of GSTSTATPLRVDY (SEQ ID NO:10);
   a CDR1 sequence of GFKITHYTMG (SEQ ID NO:1), a CDR2 sequence of RITWGGDNTIYSNSVKG (SEQ ID NO:7), and a CDR3 sequence of GSTSTATPLRVDY (SEQ ID NO:10); or
   a CDR1 sequence of GFKITHYTMG (SEQ ID NO:1), a CDR2 sequence of RITWGGDNTLYSNSVKG (SEQ ID NO:8), and a CDR3 sequence of GSTSTATPLRVDY (SEQ ID NO:10).

5. The isolated or purified antibody fragment of claim 1, comprising a sequence selected from the group consisting of:

```
                                                   (SEQ ID NO: 11)
EVQLVESGGGLVQPGGSLRLSCAASGFKITHYTMGWFRQAPGKEREFVSR

ITWGGDNTFYSNSVKGRFTISRDNSKNTLYLQMNSLRAEDTAVYYCAAGS

TSTAKPLRVDYWGQGTLVTVSS;

(SEQ ID NO: 12)
EVQLVESGGGLVQPGGSLRLSCAASGFKITHYTMGWFRQAPGKEREFVSR

ITWGGKNTFYSNSVKGRFTISRDNSKNTLYLQMNSLRAEDTAVYYCAAGS

TSTATPLRVDYWGQGTLVTVSS;

(SEQ ID NO: 13)
EVQLVESGGGLVQPGGSLRLSCAASGFKITHYTMGWFRQAPGKEREFVSR

ITWGGDDTFYSNSVKGRFTISRDNSKNTLYLQMNSLRAEDTAVYYCAAGS

TSTATPLRVDYWGQGTLVTVSS;
```

-continued (SEQ ID NO: 14)
EVQLVESGGGLVQPGGSLRLSCAASGFKITHYTMGWFRQAPGKEREFVSR

ITWGGDNTIYSNSVKGRFTISRDNSKNTLYLQMNSLRAEDTAVYYCAAGS

TSTATPLRVDYWGQGTLVTVSS;

(SEQ ID NO: 15)
EVQLVESGGGLVQPGGSLRLSCAASGFKITHYTMGWFRQAPGKEREFVSR

ITWGGDNTLYSNSVKGRFTISRDNSKNTLYLQMNSLRAEDTAVYYCAAGS

TSTATPLRVDYWGQGTLVTVSS;

and a sequence at least 90% identical thereto.

6. The isolated or purified antibody fragment of claim 1, wherein the antibody fragment is a single-domain antibody (sdAb).

7. The isolated or purified antibody fragment of claim 6, wherein the sdAb is humanized.

8. The isolated or purified antibody fragment of claim 1, wherein the antibody fragment is in a multivalent display format.

9. The isolated or purified antibody fragment of claim 8, wherein the antibody fragment is linked to a Fc fragment.

10. The isolated or purified antibody fragment of claim 9, wherein the Fc fragment is the mouse Fc2b or human Fc1.

11. The isolated or purified antibody fragment of claim 10, wherein the Fc comprises the sequence of SEQ ID NO:29.

12. The isolated or purified antibody fragment of claim 1, wherein the isolated or purified antibody fragment transmigrates the blood-brain barrier.

13. The isolated or purified antibody fragment of claim 1, wherein the antibody or fragment thereof is immobilized onto a surface.

14. The isolated or purified antibody fragment of claim 1, wherein the antibody or fragment thereof is linked to a cargo molecule.

15. The isolated or purified antibody fragment of claim 14, wherein the cargo molecule has a molecular weight in the range of about 1 kDa to about 200 kDa.

16. The isolated or purified antibody fragment of claim 14, wherein the cargo molecule is a detectable agent, a therapeutic, a drug, a peptide, a growth factor, a cytokine, a receptor trap, a chemical compound, a carbohydrate moiety, an enzyme, an antibody or fragment thereof, a DNA-based molecule, a viral vector, or a cytotoxic agent; one or more liposomes or nanocarriers loaded with a detectable agent, a therapeutic, a drug, a peptide, an enzyme, an antibody or fragment thereof, a DNA-based molecule, a viral vector, or a cytotoxic agent; or one or more nanoparticle, nanowire, nanotube, or quantum dots.

17. A composition comprising one or more than one isolated or purified antibody fragment of claim 1 and a pharmaceutically-acceptable carrier, diluent, or excipient.

18. A nucleic acid molecule encoding the isolated or purified antibody fragment of claim 1.

19. A vector comprising the nucleic acid molecule of claim 18.

* * * * *